(12) United States Patent
Hazan et al.

(10) Patent No.: US 10,751,347 B2
(45) Date of Patent: Aug. 25, 2020

(54) COMPOSITIONS COMPRISING ACIDIC EXTRACTS OF MASTIC GUM AND USES THEREOF FOR TREATING OPTIC NEUROPATHY

(71) Applicant: REGENERA PHARMA LTD., Ness Ziona (IL)

(72) Inventors: Zadik Hazan, Zichron Yaakov (IL); Andre C. B. Lucassen, Rehovot (IL); Konstantin Adamsky, Gedera (IL)

(73) Assignee: REGENERA PHARMA LTD., Ness Ziona (IL)

( * ) Notice: Subject to any disclaimer, the term of this patent is extended or adjusted under 35 U.S.C. 154(b) by 0 days.

(21) Appl. No.: 16/330,491

(22) PCT Filed: Sep. 7, 2017

(86) PCT No.: PCT/IL2017/051008
§ 371 (c)(1),
(2) Date: Mar. 5, 2019

(87) PCT Pub. No.: WO2018/047176
PCT Pub. Date: Mar. 15, 2018

(65) Prior Publication Data
US 2019/0224216 A1 Jul. 25, 2019

Related U.S. Application Data

(60) Provisional application No. 62/384,718, filed on Sep. 8, 2016.

(51) Int. Cl.
A61K 31/568 (2006.01)
A61K 31/19 (2006.01)
A61K 36/22 (2006.01)
A61K 31/569 (2006.01)
A61K 31/56 (2006.01)
A61P 27/02 (2006.01)
A61P 27/06 (2006.01)

(52) U.S. Cl.
CPC ............ A61K 31/568 (2013.01); A61K 31/19 (2013.01); A61K 31/56 (2013.01); A61K 31/569 (2013.01); A61K 36/22 (2013.01); A61P 27/02 (2018.01); A61P 27/06 (2018.01); A61K 2236/33 (2013.01)

(58) Field of Classification Search
CPC ..................... A61K 31/569; A61K 31/568
See application file for complete search history.

(56) References Cited

U.S. PATENT DOCUMENTS

| | | | |
|---|---|---|---|
| 7,048,943 B2 | 5/2006 | Barenholz et al. | |
| 9,271,949 B2 | 3/2016 | Hazan et al. | |
| 9,770,456 B2 * | 9/2017 | Hazan ................... | A61K 31/57 |
| 2005/0238740 A1 | 10/2005 | Fotinos et al. | |
| 2012/0003175 A1 | 1/2012 | Hazan | |
| 2016/0199389 A1 * | 7/2016 | Hazan ................... | A61K 31/57 |
| | | | 514/171 |
| 2018/0071351 A1 | 3/2018 | Hazan et al. | |
| 2019/0192594 A1 | 6/2019 | Hazan | |

FOREIGN PATENT DOCUMENTS

| | | |
|---|---|---|
| CN | 103656290 A | 3/2014 |
| EP | 1520585 A1 | 4/2005 |
| WO | 03092712 A1 | 11/2003 |
| WO | 2005094837 A1 | 10/2005 |
| WO | 2005112967 A2 | 12/2005 |
| WO | 2010100650 A2 | 9/2010 |
| WO | 2010100651 A2 | 9/2010 |
| WO | 2012032523 A2 | 3/2012 |
| WO | 2013186766 A1 | 12/2013 |
| WO | 2016142936 A1 | 9/2016 |

OTHER PUBLICATIONS

Gupta et al. Curr. Opin. Ophthalmol, 2007, 18(2): 110-4 (abstract).*
Aalami-Harandi et al., (2008) Efficacy of Memantine in Acute Non-Arteritic Ischemic Optic Neuropathy. Iranian Journal of Ophthalmology 20(3): 39-44.
Al-Habbal et al., (1984) A double-blind controlled clinical trial of mastic and placebo in the treatment of duodenal ulcer. Clin Exp Pharmacol Physiol 11(5): 541-544.
Allcutt et al., (1984) A qualitative comparison of the reactions of retinal ganglion cell axons to optic nerve crush in neonatal and adult mice. Developmental Brain Research 16(2): 231-240.
Allcutt et al., (1984) A quantitative comparison of the reactions of retinal ganglion cells to optic nerve crush in neonatal and adult mice. Developmental Brain Research 16(2): 219-230.
Al-Said et al., (1986) Evaluation of mastic, a crude drug obtained from Pistacia lentiscus for gastric and duodenal anti-ulcer activity. J Ethnopharmacol 15(3): 271-278.
Barton and Seoane (1956) 801. Triterpenoids. Part XXII. The constitution and stereochemistry of masticadienonic acid. J Chem Soc 0: 4150-4157.
Cioffi et al., (1995) An in vivo model of chronic optic nerve ischemia: The dose-dependent effects of endothelin-I on the optic nerve microvasculature. Current Eye Research 14(12): 1147-1153.
Cone et al., (2012) The effects of anesthesia, mouse strain and age on intraocular pressure and an improved murine model of experimental glaucoma. Exp Eye Res 99: 27-35.
Giner-Larza et al., (2002) Anti-inflammatory triterpenes from Pistacia terebinthus galls. Planta Med 68(4): 311-315.
Kalesnykas et al., (2007) The expression of heat shock protein 27 in retinal ganglion and glial cells in a rat glaucoma model. Neuroscience 150(3): 692-704.
Kawasaki et al., (2002) Protective effect of arachidonic acid on glutamate neurotoxicity in rat retinal ganglion cells. Investigative Ophthalmology & Visual Science 43(6): 1835-1842.
Orgül et al., (1996) An endothelin-1-induced model of chronic optic nerve ischemia in rhesus monkeys. Journal of Glaucoma 5(2): 135-138.

(Continued)

Primary Examiner — Rei Tsang Shiao
(74) Attorney, Agent, or Firm — Rothwell, Figg, Ernst & Manbeck, P.C.

(57) ABSTRACT

The invention relates to compositions and formulations comprising isolated acidic fraction of mastic gum and uses thereof for treating optic neuropathy conditions.

20 Claims, 2 Drawing Sheets

(56) References Cited

OTHER PUBLICATIONS

Marner et al., (1991) Triterpenoids from gum mastic, the resin of Pistacia lentiscus. Phytochemistry 30(11): 3709-3712.
Otori (2008) Use of purified retinal ganglion cells for an in vitro model to study glaucoma. Mechanisms of the Glaucomas: 601-607.
Paraschos et al., (2007) In vitro and in vivo activities of Chios mastic gum extracts and constituents against Helicobacter pylori. Antimicrob Agents Chemother 51(2): 551-559.
Ragauskas et al., (2014) Early retinal function deficit without prominent morphological changes in the R6/2 mouse model of Huntington's disease. PLoS One 9(12): e113317; 24 pages.
Sappington et al., (2010) The microbead occlusion model: a paradigm for induced ocular hypertension in rats and mice. Investigative Ophthalmology & Visual science 51(1): 207-216.
Seoane (1956) 802. Further crystalline constituents of gum mastic. J Chem Soc 0: 4158-4160.

* cited by examiner

COMPOSITIONS COMPRISING ACIDIC EXTRACTS OF MASTIC GUM AND USES THEREOF FOR TREATING OPTIC NEUROPATHY

CROSS REFERENCE TO RELATED APPLICATION

This application is a 35 U.S.C. 371 National Phase Entry Application from PCT/IL2017/051008, filed Sep. 7, 2017, which claims the benefit of U.S. Provisional Patent Application No. 62/384,718 filed on Sep. 8, 2016, the disclosures of which are incorporated herein in their entirety by reference.

FIELD OF THE INVENTION

The invention relates to therapeutic uses of isolated acidic fractions of mastic gum for treating optic neuropathy, such as optical nerve ischemia and glaucoma. More particularly, the invention relates to methods of treating such optic neuropathy conditions using compositions comprising isolated acidic fractions of mastic gum.

BACKGROUND OF THE INVENTION

Mastic, also known as gum mastic or mastic gum, is a tree resin obtained as an exudate from *Pistacia lentiscus* L., a member of the family Anacardiaceae. Mastic was used in the ancient Mediterranean world for treating various conditions, such as, gastrointestinal disorders such as gastralgia, dyspepsia and peptic ulcer. Oral administration of mastic to human patients with duodenal ulcer and to experimental rats with induced gastric and duodenal ulcers has been disclosed to have therapeutic effects (Al-Habbal et al (1984) Clin Exp Pharmacop Physio 11(5):541-4; Said et al (1986) J Ethnopharmacol 15(3):271-8).

U.S. Patent Application Publication No 2005/0238740 is directed to Use of mastic and its components for the control of microbial infections.

EP Patent Application No. 1520585 discloses use of a product obtained from a plant of the genus *Pistacia* for the manufacture of a medicament for treating or preventing cancer.

International Patent Application Publication No. WO 2005/112967 discloses the purification from mastic of anti-cancer material having anti-proliferative effects, which is found in a soluble fraction obtained by suspending mastic in a solvent selected from a non-acidic, aliphatic hydrocarbon, an aqueous solution containing at least 25% of a water-soluble, non-acidic, aliphatic hydrocarbon, or a combination thereof, and removing the insoluble fraction.

International Patent Application Publication No. WO 2010/100650 to some of the inventors of the present invention, is directed to therapeutic uses of mastic gum fractions.

International Patent Application Publication No. WO 2010/100651 to some of the inventors of the present invention, is directed to compositions of polymeric myrcene.

International Patent Application Publication No. WO 2012/032523 to some of the inventors of the present invention, is directed to compositions comprising acidic extracts of mastic gum.

International Patent Application Publication No. WO 2005/094837 is directed to Use of masticadienonic acid as inhibitor of DNA polymerase-beta, used for treating cancers, tumors and neurodegenerative diseases.

Marner et al (1991) disclose identification of various triterpenoids from gum mastic of *P. lentiscus* (Marner et al (1991) Phytochemistry, 30, 3709-3712).

Giner-Larza et al (2002) disclose anti-inflammatory triterpenes from *pistacia* terebinthus galls (Planta Med (2002), 68, 311-315).

The optic nerve contains axons of nerve cells that emerge from the retina, leave the eye at the optic disc, and go to the visual cortex where input from the eye is processed into vision. Optic neuropathy refers to damage to the optic nerve due to any cause. Damage and death of these nerve cells, leads to characteristic features of optic neuropathy. The main symptom is loss of vision, with colors appearing subtly washed out in the affected eye. On medical examination, the optic nerve head can be visualized by an ophthalmoscope. A pale disc is characteristic of long-standing optic neuropathy. In many cases, only one eye is affected and patients may not be aware of the loss of color vision until the doctor asks them to cover the healthy eye.

Optic neuropathy can result from various reasons, such as, Ischemic optic neuropathy, Optic neuritis, Compressive optic neuropathy, Infiltrative optic neuropathy, Traumatic optic neuropathy, mitochondrial optic neuropathy, Nutritional optic neuropathies, toxic optic neuropathies, hereditary optic neuropathies, and the like. Very few treatments of optical neuropathy are currently used, and most have a limited effect on specific type of optic neuropathy.

Thus, there is a need in the art for compositions that are useful and effective in treating conditions of optical neuropathy, resulting from various reasons. The art does not provide any teaching that isolated acidic fractions of mastic gum can be used for treating optical neuropathy conditions.

SUMMARY OF THE INVENTION

The present invention provides pharmaceutical compositions comprising an isolated acidic fraction of mastic gum, which contains acidic compounds that are soluble in both polar and non-polar organic solvents, and which have optical nerve neuro-regenerative properties and methods of using same for treating optic neuropathy conditions, such as, optical nerve ischemic condition, Glaucoma, and the like. More specifically, compositions comprising isolated acidic fractions extracted from mastic gum are disclosed to be able to treat related conditions, such as those resulting from ischemia and/or trauma to the optic nerve.

In some embodiments, the present invention is based in part on the unexpected discovery that isolated acidic fractions of mastic gum exhibit such enhanced optical-nerve regenerative biological activity. The isolated acidic fractions of the invention exhibit a variety of beneficial biological activities which may be exploited for various therapeutic applications.

According to some embodiments, there is thus provided the use of a composition comprising isolated acidic fractions of mastic gum and a pharmaceutically acceptable carrier, for treating an optic neuropathy condition.

According to some embodiments, there is provided a method of treating an optic neuropathy condition in a subject in need thereof, the method comprising administering a composition comprising an effective amount of an isolated acidic fraction of mastic gum, and a pharmaceutically acceptable carrier, wherein the fraction is characterized in that it is soluble in at least one polar organic solvent and in at least one non-polar organic solvent, and wherein said fraction is substantially devoid of compounds which are soluble in said polar organic solvent but insoluble in said non-polar organic solvent.

In some embodiments, the acidic fraction is obtained from an isolated fraction of mastic gum that is soluble in at least one polar organic solvent and at least one non-polar organic solvent by an acid-base extraction, thereby separating the isolated acidic fraction from the non-acidic fraction of mastic gum that is soluble in at least one polar organic solvent and one non-polar organic solvent.

In some embodiments, the isolated acidic fraction comprises at least two of: masticadienolic acid; masticadienonic acid; isomasticadienonic acid, isomasticadienolic acid, 3-O-acetyl-masticadienolic acid, 3-O-acetyl-epimasticadienolic acid, 3-O-acetyl-isomasticadienolic acid, 3-O-acetyl-epi-isomasticadienolic acid, oleanonic acid and moronic acid.

According to further embodiments, there is provided a use of an isolated acidic fraction of mastic gum, for the preparation of a medicament for treating optic neuropathy.

According to another aspect, there is provided an isolated acidic fraction of mastic gum, for use in treating optic neuropathy.

According to some embodiments, there is provided a pharmaceutical composition comprising an isolated acidic fraction of mastic gum and a pharmaceutically acceptable carrier, for use in treating optic neuropathy.

In various embodiments, the composition may be administered by parenteral route. According to some embodiments the route of administration may be via parenteral injection. In various embodiments, the step of administering is carried out by a parenteral route selected from the group consisting of intravenous (i.v.), intramuscular, subcutaneous (sc), intradermal, intraperitoneal, intraarterial, intracerebral, intracerebroventricular, intraosseous, intraocular, intravitreal, and intrathecal.

In some embodiments, the optic neuropathy condition comprises any condition in which the optic nerve is damaged. In some embodiments, the optic neuropathy condition may be selected from such conditions as, but not limited to: traumatic neuropathy (that may result from any type of trauma to the optic nerve); ischemic neuropathy (such as, for example, Nonarteritic Anterir Ischemic Optic neuropathy (NAION), Anterior ischemic optic neuropathy (AION), Posterior ischemic optic neuropathy); Radiation optic neuropathy (RON)), Glaucoma, Optic neuritis, Compressive optic neuropathy, Infiltrative optic neuropathy, Mitochondrial optic neuropathy, Nutritional optic neuropathies, toxic optic neuropathies, Hereditary optic neuropathy and the like; or combinations thereof. Each possibility is a separate embodiment.

In some embodiments, the optic neuropathy condition is resulting from or associated with damage to the optical nerve as a result of deposition of lipoproteinaceous substances in the optic nerve.

In some embodiments, the optic neuropathy condition is resulting from or associated with damage to the optical nerve as a result of deposition of lipoproteinaceous substances in the optic nerve, wherein the deposition of lipoproteinaceous substances is the result of a storage disease.

In some embodiments, the optic neuropathy condition is resulting from or associated with damage to the optical nerve as a result of deposition of lipoproteinaceous substances in the optic nerve, wherein the deposition of lipoproteinaceous substances is the result of a storage disease, and wherein the lipoproteinaceous substance is lipofuscin.

According to some embodiments, the present invention further provides compositions comprising isolated compounds from the isolated acidic fraction of mastic gum, having therapeutic activity. In some embodiments, the compositions may include a plurality of isolated compounds selected from the individual acidic compounds found in the acidic fraction of mastic gum according to the invention. According to some embodiments, the composition includes at least three isolated compounds selected from masticadienonic acid, isomasticadienonic acid, masticadienolic acid, isomasticadienolic acid, 3-O-acetyl-masticadienolic acid, 3-O-acetyl-epimasticadienolic acid, 3-O-acetyl-isomasticadienolic acid, 3-O-acetyl-epi-isomasticadienolic acid, oleanonic acid, moronic acid and 3-oxo-lup-20(29)-en-28-oic acid. According to some embodiments, the composition includes at least three isolated compounds selected from masticadienonic acid, isomasticadienonic acid, masticadienolic acid, isomasticadienolic acid, 3-O-acetyl-masticadienolic acid, 3-O-acetyl-epimasticadienolic acid, 3-O-acetyl-isomasticadienolic acid, 3-O-acetyl-epi-isomasticadienolic acid, oleanonic acid, moronic acid. According to some embodiments, the composition includes at least three isolated compounds selected from masticadienonic acid, isomasticadienonic acid, masticadienolic acid, 3-O-acetyl-masticadienolic acid, 3-O-acetyl-isomasticadienolic acid, oleanonic acid and moronic acid. In some embodiments, the compositions include at least masticadienonic acid, isomasticadienonic acid and oleanonic acid. Such compositions unexpectedly exhibit a synergistic effect, whereby the combination of compounds exhibit a markedly improved therapeutic effect in the treatment of optic neuropathy conditions, as compared to the individual compounds alone.

According to some embodiments, the composition includes at least two isolated compounds selected from masticadienonic acid, isomasticadienonic acid, masticadienolic acid, isomasticadienolic acid, 3-O-acetyl-masticadienolic acid, 3-O-acetyl-epimasticadienolic acid, 3-O-acetyl-isomasticadienolic acid, 3-O-acetyl-epi-isomasticadienolic acid, oleanonic acid, moronic acid and 3-oxo-lup-20(29)-en-28-oic acid. According to some embodiments, the composition includes at least two isolated compounds selected from masticadienonic acid, isomasticadienonic acid, masticadienolic acid, isomasticadienolic acid, 3-O-acetyl-masticadienolic acid, 3-O-acetyl-epimasticadienolic acid, 3-O-acetyl-isomasticadienolic acid, 3-O-acetyl-epi-isomasticadienolic acid, oleanonic acid and moronic acid. According to some embodiments, the composition includes at least two isolated compounds selected from masticadienonic acid, isomasticadienonic acid, masticadienolic acid, 3-O-acetyl-masticadienolic acid, 3-O-acetyl-isomasticadienolic acid, oleanonic acid, moronic acid. In some exemplary embodiments, the compositions include at least masticadienonic acid and isomasticadienonic acid. Such compositions unexpectedly exhibit a synergistic effect, whereby the combination of compounds exhibit a markedly improved therapeutic effect in the treatment of optic neuropathy conditions, as compared to the individual compounds alone.

The mastic acidic fraction according to embodiments of the invention may be distinguished over mastic fractions disclosed in the prior art, as its preparation involves use of both a polar solvent and a non-polar solvent, whereas the prior art teaches use of polar solvents only. Acidic fractions prepared by using only polar solvents contain compounds that are not soluble in apolar solvents such as hexane, whereas these compounds are not present in the acidic fraction of the current invention. Accordingly, the fractions of the invention comprise a combination of compounds which differs from that disclosed in the prior art. Moreover, the inventors of the present invention have discovered that the acidic fraction of the invention unexpectedly possesses unexpected therapeutic activities that are not suggested by the prior art, in particular, treating a range of optic neuropathy conditions.

The teachings of the present invention have been exemplified with mastic gum extracts prepared by a three-step extraction procedure, so as to obtain an acidic fraction that is soluble in both a polar solvent and a non-polar solvent, and wherein material from the mastic gum that is soluble in the polar solvent but remains insoluble in the non-polar solvent is eliminated. In further embodiments, main compounds of the isolated acidic fraction have been isolated and identified. Various combinations of some of these compounds exhibit an unexpected synergistic effect in the treatment of optic neuropathy conditions.

It is to be further understood that the biological activity of the fractions and compositions disclosed herein is inhibited by the presence of certain compounds that are be present in acidic fractions that have been prepared without applying the first two extraction steps as disclosed herein.

According to some embodiments, the present invention provides a composition for use in treating optic neuropathy conditions, the composition comprising an effective amount of an isolated acidic fraction of mastic gum, and a pharmaceutically acceptable carrier; wherein the fraction is characterized in that it is soluble in at least one polar organic solvent and soluble in at least one non-polar organic solvent, and wherein said fraction is substantially devoid of compounds which are soluble in said polar organic solvent but insoluble in said non-polar organic solvent.

In some embodiments, the composition may be obtained by a process comprising the steps of:
(a) treating mastic gum with a polar organic solvent;
(b) isolating a fraction soluble in said polar organic solvent;
(c) optionally removing said polar organic solvent;
(d) treating the soluble fraction obtained in step (b) or (c) with a non-polar organic solvent,
(e) isolating a fraction soluble in said non-polar organic solvent;
(f) optionally removing said non-polar organic solvent;
(g) dissolving the fraction obtained in step (f) in an organic solvent;
(h) treating the solution obtained in step (g) with a basic solution so as to obtain a basic fraction; and
(i) acidifying the basic fraction obtained in step (h) with an acid solution;

In some embodiments, steps (d) to (f) may precede steps (a) to (c).

In some embodiments, the treatment with a basic solution (basifying) in step (h) comprises extracting the solution obtained in step (g) with one or more suitable basic aqueous solutions; or contacting the solution obtained in step (g) with a basic ion exchange resin.

In some embodiments, step (h) comprises contacting the solution obtained in step (g) with a basic ion exchange resin, and thereafter removing the basic ion exchange resin by filtration. In these embodiments, step (i) comprises treating the basic ion exchange resin with an acidic solution.

In some embodiments, the process further comprises the steps of
(j) extracting the acidified fraction obtained in step (i) with an organic solvent;
k) optionally contacting the organic fraction obtained in step (j) with a drying agent so as to remove remaining water;
(l) removing organic solvent and/or excess acid from the fraction obtained in any of steps (i), (j) or (k); and
(m) dissolving the isolated fraction obtained in step (l) in a carrier.

In some embodiments, steps (a) to (c) are carried out prior to steps (d) to (f); or steps (d) to (f) are carried out prior to steps (a) to (c). In some embodiments, (a) to (c) and/or steps (d) to (f) are repeated for a multiplicity of cycles.

In some embodiments, any of steps (c), (f) and (l) comprise removing the solvent by a means selected from the group consisting of rotary evaporation, application of high vacuum and a combination thereof.

In some embodiments, step (h) comprises extracting the solution obtained in step (g) with a basic aqueous solution, and collecting the organic fraction thus obtained. In some embodiments, the process further comprises combining the organic fraction obtained from step (h) with a fraction obtained in any of steps (i), (j) or (k).

In some embodiments, the organic fraction obtained in step (h) is combined with a fraction obtained in any of steps (i), (j) or (k) in an amount in the range from about 0.1% to about 50% of the organic fraction obtained from step (h). In some embodiments, the amount is in the range from 0.5 to 50%; or 2 to 25%; or 0.1 to 10%.

Polar organic solvents suitable for use in the invention may be selected from an alcohol, an ether, an ester, an amide, an aldehyde, a ketone, a nitrile, and combinations thereof.

Specific examples of suitable polar organic solvents include methanol, ethanol, propanol, isopropanol, 1-butanol, 2-butanol, sec-butanol, t-butanol, 1-pentanol, 2-pentanol, 3-pentanol, neopentanol, 3-methyl-1-butanol, 2-methyl-1-butanol, 3-methyl-2-butanol, 2-methyl-2-butanol, ethyleneglycol, ethyleneglycol monomethyl ether, diethyl ether, methylethyl ether, ethylpropyl ether, methylpropyl ether, 1,2-dimethoxyethane, tetrahydrofuran, dihydrofuran, furan, pyran, dihydropyran, tetrahydropyran, methyl acetate, ethyl acetate, propyl acetate, acetaldehyde, methylformate, ethylformate, ethyl propionate, methyl propionate, dichloromethane, chloroform, dimethylformamide, acetamide, dimethylacetamide, N-methylpyrrolidone, acetone, ethylmethyl ketone, diethyl ketone, acetonitrile, propionitrile, and combinations thereof.

In some embodiments, the polar organic solvent is selected from methanol and ethanol or a combination thereof. In some embodiments, the polar solvent is ethanol.

Non-polar organic solvents suitable for use in the invention may be selected from acyclic or cyclic, saturated or unsaturated aliphatic hydrocarbons and aromatic hydrocarbons, each of which is optionally substituted by one or more halogens, and combinations thereof. In some embodiments, the non-polar organic solvent is selected from C5-C10 alkanes, C5-C10 cycloalkanes, C6-C14 aromatic hydrocarbons and C7-C14 perfluoroalkanes, and combinations thereof.

In some embodiments, the non-polar organic solvent is selected from pentanes, hexanes, heptanes, octanes, nonanes, decanes, cyclopentane, cyclohexane, cycloheptane, benzene, toluene, xylene, and isomers and mixtures thereof.

In some embodiments, the C5-C10 alkane is selected from the group consisting of pentane, hexane, heptane, octane, nonane, decane, cyclohexane, and isomers and mixtures thereof. In some embodiments, the non-polar organic solvent is hexane.

In some embodiments, the organic solvent in step (g) and in step (j) is independently selected from the group consisting of dialkyl ethers, alkyl-aryl ethers, diaryl ethers, esters, ketones, halogenated hydrocarbons, C5-C14 aromatic hydrocarbons, C5-C14 perfluoroalkanes.

In some embodiments, the suitable organic solvent in step (g) and in step (j) is the same or different.

In some embodiments, the organic solvent comprises a dialkyl ether. In some embodiments, the organic solvent is diethyl ether.

In some embodiments, the polar organic solvent comprises ethanol, the non-polar organic solvent comprises hexane and the organic solvent comprises diethyl ether.

In some embodiments, step (h) comprises basifying with a basic aqueous solution. In some embodiments, the basic aqueous solution is prepared by dissolving an inorganic base in water.

In some embodiments, the inorganic base is selected from the group consisting of sodium carbonate, sodium hydroxide, potassium carbonate potassium hydroxide, ammonium hydroxide, sodium bicarbonate, sodium phosphate, lithium hydroxide, lithium carbonate, and potassium phosphate.

In some embodiments, the inorganic base is sodium carbonate. In some embodiments, the concentration of the sodium carbonate in water is in the range from 2 to 20% w/w. In some embodiments, the concentration of sodium carbonate is in the range from 3 to 15% w/w. In some embodiments, the concentration of sodium carbonate is about 5% w/w.

In some embodiments, the inorganic base is sodium hydroxide.

In some embodiments, the basic aqueous solution is prepared by dissolving a water-soluble organic base in water.

In some embodiments, the first inorganic base is about 5% w/w aqueous sodium carbonate, followed by about 4% w/w aqueous sodium hydroxide.

In some embodiments, the basifying in step (h) comprises contacting the solution obtained in step (g) with a basic ion exchange resin. In some embodiments, the basic ion exchange resin comprises styrene divinylbenzene, polyacrylic or formophenolic copolymers.

In some embodiments, basifying the solution is done to a pH of above about 7.

In some embodiments, basifying the solution is done to a pH range of 8-10.

In some embodiments, basifying the solution is done to a pH range of 10-13.

In some embodiments, basifying the solution is done to a pH of >13.

In some embodiments, the acidic solution in step (i) comprises an acidic aqueous solution or an acidic non-aqueous solution.

In some embodiments, the acidic aqueous solution in step (i) is prepared by dissolving an inorganic acid in water or by diluting a concentrated mineral acid solution.

In some embodiments, the acidic aqueous solution is a solution of hydrochloric acid or phosphoric acid.

In some embodiments, the acidic aqueous solution is a solution of hydrochloric acid.

In some embodiments, the acidic aqueous solution in step (i) is prepared by dissolving an organic acid in water or by diluting a concentrated mineral acid solution.

In some embodiments, acidifying is done to a pH of below about 7. In some embodiments, acidifying is done to a pH of below about 6. In some embodiments, acidifying is done to a pH of below about 5. In some embodiments, acidifying is done to a pH of below about 4. In some embodiments, acidifying is done to a pH of below about 3.

In some embodiments, acidification is done to a pH in the range of 1-3.

In some embodiments, the acidic non-aqueous solution in step (i) is prepared by dissolving an organic acid in a non-aqueous organic solvent selected from an alcohol, an ester, an ether, an amide or mixtures thereof. In some embodiments, the non-aqueous solvent is methanol or ethanol or a mixture thereof.

In some embodiments, the organic acid is selected from the group consisting of formic acid, acetic acid, propionic acid, citric acid, tartaric acid, methane sulphonic acid, and para-toluenesulphonic acid.

In some embodiments, the drying agent used in step (k) is selected from the group of sodium sulfate, magnesium sulfate, calcium sulfate, calcium chloride, magnesium chloride, potassium sulfate.

In some embodiments, the composition is substantially devoid of terpene compounds which are soluble in said polar organic solvent and insoluble in said non-polar organic solvent.

In some embodiments, the composition comprises from about 0.01 to about 25% (w/w) of the isolated acidic fraction of mastic gum, based on the total weight of the composition. In some embodiments, the composition comprises from about 0.01 to about 12% (w/w) of the isolated acidic fraction of mastic gum, based on the total weight of the composition.

In some embodiments, the isolated acidic fraction comprises at least one of: masticadienonic acid, masticadienolic acid, isomasticadienonic acid, isomasticadienolic acid, 3-O-acetyl-masticadienolic acid, 3-O-acetyl-epimasticadienolic acid, 3-O-acetyl-isomasticadienolic acid, 3-O-acetyl-epi-isomasticadienolic acid, oleanonic acid, moronic acid, and 3-oxo-lup-20(29)-en-28-oic acid. Each possibility is a separate embodiment of the invention.

In some embodiments, the isolated acidic fraction comprises at least one of: masticadienonic acid, masticadienolic acid, isomasticadienonic acid, isomasticadienolic acid, 3-O-acetyl-masticadienolic acid, 3-O-acetyl-epimasticadienolic acid, 3-O-acetyl-isomasticadienolic acid, 3-O-acetyl-epi-isomasticadienolic acid, oleanonic acid and moronic acid. Each possibility is a separate embodiment of the invention.

In some embodiments, the isolated acidic fraction further comprises at least one of: oleanolic acid, ursonic acid, and ursolic acid. Each possibility is a separate embodiment of the invention.

In some embodiments, the isolated acidic fraction may be substantially devoid of essential oils.

In some embodiments, the isolated acidic fraction comprises at least one terpenoic acid. In some embodiments, the isolated acidic fraction comprises at least one triterpenoic acid. In some embodiments, the at least one terpenoic acid comprises at least one triterpenoic acid. In some embodiments, the at least one triterpenoic acid is selected from the group consisting of masticadienolic acid, isomasticadienonic acid, isomasticadienolic acid, 3-O-acetyl-masticadienolic acid, 3-O-acetyl-epimasticadienolic acid, 3-O-acetyl-isomasticadienolic acid, 3-O-acetyl-epi-isomasticadienolic acid, oleanonic acid, moronic acid, 3-oxo-lup-20(29)-en-28-oic acid and a combination thereof. Each possibility is a separate embodiment of the invention.

In some embodiments, the at least one terpenoic acid is in monomeric form. In some embodiments, the at least one terpenoic acid is in an oligomeric form. In some embodiments, the oligomeric form is selected from the group consisting of a dimer, a trimer, and a combination thereof. Each possibility is a separate embodiment of the invention.

In some embodiments, the isolated acidic fraction comprises a combination of monomeric and dimeric triterpenoic acids. In some embodiments, the isolated acidic fraction comprises a combination of monomeric, dimeric and trimeric triterpenoic acids.

In some embodiments, the composition comprises at least one of: masticadienonic acid, masticadienolic acid, isomasticadienonic acid, isomasticadienolic acid, 3-O-acetyl-masticadienolic acid, 3-O-acetyl-epimasticadienolic acid, 3-O-acetyl-isomasticadienolic acid, 3-O-acetyl-epiisomasticadienolic acid, oleanonic acid, moronic acid, and 3-oxo-lup-20(29)-en-28-oic acid. Each possibility is a separate embodiment of the invention.

In some embodiments, the composition further comprises at least one of: oleanolic acid, ursonic acid, and ursolic acid. Each possibility is a separate embodiment of the invention.

In some embodiments, the composition comprises at least one terpenoic acid. Embodiments of terpenoic acids are as hereinbefore described.

In some embodiments, the composition comprises at least one triterpenoic acid. Embodiments of triterpenoic acids are as hereinbefore described.

In some embodiments, the mastic gum is derived from a plant classified in the family Anacardiaceae. Suitable plants include those classified in a genus selected from the group consisting of *Pistacia, Pinus, Picea, Juniperus, Alsies, Larix, Antirrhinum, Boswellia, Citrus* and *Gynura*. In some embodiments, suitable plants are selected from the genus *Pistacia*. In some embodiments, the species of *Pistacia* is selected from the group consisting of *P. lentiscus, P. atlantica, P. palestina, P. saportae, P. terebinthus, P. vera* and *P. integerrima*. In some embodiments, the species of *Pistacia* is *Pistacia lentiscus* var. Chia. In some embodiments, the species of *Pistacia* is *Pistacia lentiscus* L. In some embodiments, the species of *Pistacia* is *Pistacia lentiscus* L. var. *latifolius* Coss.

In some embodiments, the isolated acidic fraction is derived from a plant material selected from the group consisting of resin, leaves, twigs, roots, flowers, seeds, buds, bark, nuts and roots.

In some embodiments, the isolated acidic fraction of mastic gum is obtained by a process comprising the steps of:
(a) treating mastic gum with a polar organic solvent;
(b) isolating a fraction soluble in said polar organic solvent;
(c) optionally removing said polar organic solvent;
(d) treating the soluble fraction obtained in step (b) or (c) with a non-polar organic solvent,
(e) isolating a fraction soluble in said non-polar organic solvent;
(f) optionally removing said non-polar organic solvent;
(g) dissolving the fraction obtained in step (f) in an organic solvent;
(h) treatment of the solution obtained in step (g) with a basic solution so as to obtain a basic fraction;
(i) acidifying the basic fraction obtained in step (i) with an acid solution;
(j) extracting the acidified fraction obtained in step (i with an organic solvent;
(k) optionally contacting the organic fraction obtained in step (k) with a drying agent so as to remove remaining water;
(l) removing organic solvent and/or excess acid from the fraction obtained in any of steps (i), (j) or (k); and
(m) dissolving the isolated fraction obtained in step (l) in a carrier.

In additional embodiments, the invention provides a pharmaceutical composition comprising at least one triterpenoic acid; and a pharmaceutically acceptable carrier. In some embodiments, the at least one triterpenoic acid is selected from the group consisting of masticadienolic acid, isomasticadienonic acid, isomasticadienolic acid, 3-O-acetyl-masticadienolic acid, 3-O-acetyl epimasticadienolic acid, 3-O-acetyl isomasticadienolic acid, 3-O-acetyl-epi-isomasticadienolic acid, masticadienonic acid, oleanonic acid, moronic acid, 3-oxo-lup-20(29)-en-28-oic acid and a combination thereof. Each possibility is a separate embodiment of the invention.

According to some embodiments, the current invention provides a pharmaceutical composition consisting essentially of isomasticadienonic acid and masticadienonic acid as the pharmaceutically active ingredients; and a pharmaceutically acceptable carrier. The combined presence of both compounds results in an enhanced/synergistic effect with respect to the composition's efficacy in the treatment of optic neuropathy condition, when compared with the efficacy of the individual compounds. Either one of isomasticadienonic acid and masticadienonic acid may be isolated from a natural source such as mastic gum, or may be the product of a chemical synthesis.

In some embodiments, the ratio between the isomasticadienonic acid and masticadienonic acid is about 1:1 w/w.

According to some embodiments, the current invention provides a pharmaceutical composition consisting essentially of oleanonic acid, isomasticadienonic acid and masticadienonic acid as the sole pharmaceutically active ingredients; and a pharmaceutically acceptable carrier for use in treating optical neuropathy.

According to some embodiments, the current invention provides a pharmaceutical composition consisting essentially of isomasticadienonic acid and masticadienonic acid as the sole pharmaceutically active ingredients; and a pharmaceutically acceptable carrier, for treating an optic neuropathy condition. The combined presence of these two compounds results in a synergistic effect with respect to composition's efficacy in the treatment of optic neuropathy conditions when compared with the efficacy of the individual compounds.

Any one of oleanonic acid, isomasticadienonic acid and masticadienonic acid may be either isolated from a natural source, such as mastic gum, or may be the product of a chemical synthesis. In some embodiments, the ratio between the isomasticadienoic acid and masticadienonic acid and oleanonic acid is about 1:1:1 w/w/w.

In some embodiments, the at least one triterpenoic acid is a monomer. In some embodiments, the composition comprises monomers of oleanonic acid and moronic acid. In some embodiments, the monomers of oleanonic acid and moronic acid are the products of chemical synthesis reactions.

In some embodiments, the at least one triterpenoic acid comprises an oligomeric form. In some embodiments, the oligomeric form is selected from the group consisting of a dimer, a trimer, and a combination thereof. Each possibility is a separate embodiment of the invention. In some embodiments, the oligomeric form is a dimer. In some embodiments, the at least one triterpenoic acid is the product of a chemical synthesis.

In some embodiments, the at least one triterpenoic acid comprising an oligomeric form is the product of a chemical synthesis. In some embodiments, the at least on triterpenoic acid is a dimeric form and is the product of a chemical synthesis.

In some embodiments, the at least one triterpenoic acid is derived from a natural source, in particular a plant source.

In some embodiments, the composition comprises a combination of different triterpenoic acids, wherein at least one triterpenoic acid is the product of a chemical synthesis and at least one other triterpenoic acid is derived from a plant source.

Natural sources include plants classified in the family Anacardiaceae. Suitable plants include those classified in a genus selected from the group consisting of *Pistacia, Pinus, Picea, Juniperus, Alsies, Larix, Antirrhinum, Boswellia, Citrus* and *Gynura*. In some embodiments, suitable plants are selected from the genus *Pistacia*. In some embodiments, the species of *Pistacia* is selected from the group consisting of *P. lentiscus, P. atlantica, P. palestina, P. saportae, P. terebinthus, P. vera* and *P. integerrima*. In some embodiments, the species of *Pistacia* is *Pistacia lentiscus* L.

In some embodiments, the natural source is a plant material selected from the group consisting of resin, leaves, twigs, roots, flowers, seeds, buds, bark, nuts and roots.

In some embodiments, the natural source is a plant classified in a genus selected from the group consisting of *Ocimum*, *Laurus* and *Lavendula*.

In some embodiments, the pharmaceutically acceptable carrier comprises a hydrophobic carrier. In some embodiments, the hydrophobic carrier comprises at least one oil. In some embodiments, the oil is selected from the group consisting of a mineral oil, a vegetable oil and combinations thereof. In some embodiments, the vegetable oil is selected from the group consisting of cottonseed oil, olive oil, almond oil, canola oil, coconut oil, corn oil, grape seed oil, peanut oil, saffron oil, sesame oil, soybean oil, and combinations thereof. In some embodiments, the mineral oil is light mineral oil. In some embodiments, the hydrophobic carrier comprises at least one wax. In some embodiments, the hydrophobic carrier comprises a combination of at least one oil and at least one wax. In some embodiments, the composition is a pharmaceutical composition.

In some embodiments, the subject is a human. In some embodiments, the subject is a non-human mammal.

In some embodiments, there is provided a method of treating an optic neuropathy condition, the method comprising administering a composition consisting essentially of a mixture of triterpenoids comprising at least two triterpenoic acids, selected from the group consisting of: masticadienonic acid, isomasticadienonic acid, isomasticadienolic acid, masticadienolic acid, 3-O-acetyl-masticadienolic acid, 3-O-acetyl-epimasticadienolic acid, 3-O-acetyl-isomasticadienolic acid, 3-O-acetyl-epi-isomasticadienolic acid, oleanonic acid, moronic acid and combinations thereof; and a pharmaceutically acceptable carrier.

In some embodiments, there is provided a use of a composition comprising an effective amount of an isolated acidic fraction of mastic gum, and a pharmaceutically acceptable carrier; for treating an optic neuropathy condition, wherein the fraction is characterized in that it is soluble in at least one polar organic solvent and in at least one non-polar organic solvent, and wherein said fraction is substantially devoid of compounds which are soluble in said polar organic solvent but insoluble in said non-polar organic solvent.

In some embodiments, there is provided a composition consisting essentially of a mixture of triterpenoids comprising at least two triterpenoic acids, selected from the group consisting of: masticadienonic acid, isomasticadienonic acid, isomasticadienolic acid, masticadienolic acid, 3-O-acetyl masticadienolic acid, 3-O-acetyl-epimasticadienolic acid, 3-O-acetyl-isomasticadienolic acid, 3-O-acetyl-epi-isomasticadienolic acid, oleanonic acid, moronic acid and combinations thereof; and a pharmaceutically acceptable carrier, for use in treating an optic neuropathy condition in a subject in need thereof.

In some embodiments, there is provided a kit comprising: a pharmaceutical composition comprising an effective amount of an isolated acidic fraction of mastic gum and a pharmaceutically acceptable carrier; and instructions for using the kit for the treatment of optic neuropathy condition in a subject in need thereof.

In some embodiments, there is provided a kit comprising: a pharmaceutical composition consisting essentially of a mixture of triterpenoids comprising at least two triterpenoic acids, selected from the group consisting of: masticadienonic acid, isomasticadienonic acid, isomasticadienolic acid, masticadienolic acid, 3-O-acetyl masticadienolic acid, 3-O-acetyl-epimasticadienolic acid, 3-O-acetyl-isomasticadienolic acid, 3-O-acetyl-epi-isomasticadienolic acid, oleanonic acid, moronic acid and combinations thereof and a pharmaceutically acceptable carrier; and instructions for using the kit for the treatment of optic neuropathy condition in a subject in need thereof.

Other objects, features and advantages of the present invention will become clear from the following description and drawings.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION OF THE INVENTION

Figure 1:
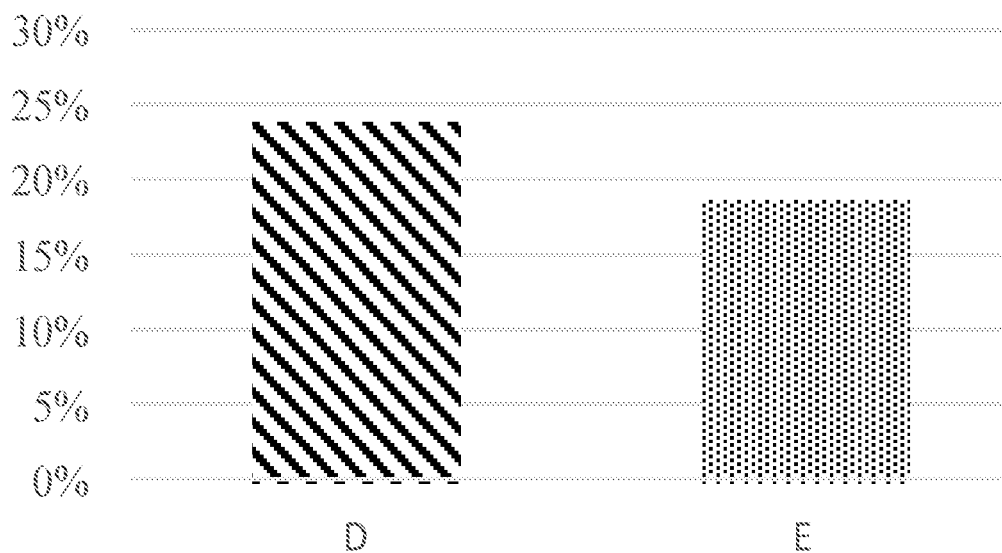
FIG. 1—Bar graphs showing pERG measurements relative change in mean amplitude in treated rats (Eye-laser irradiated) performed at follow-up day 28 as compared to control vehicle-treated group.

According to some embodiments, there are provided compositions comprising isolated acidic fractions extracted from mastic gum, compounds comprised therein, and uses thereof for treating optical neuropathy.

It is herein disclosed for the first time that the disclosed isolated acidic fractions of mastic gum as described herein, may be employed as an active ingredient in a pharmaceutical composition for treating optical neuropathy, (resulting from various consequences), which are severe conditions that may lead to loss of vision in afflicted subjects.

Definitions

As used herein, the terms "mastic", "mastic resin", "gum mastic" and "mastic gum", are used interchangeably to refer to a tree resin (also known as an oleoresin) obtained as an exudate from any tree classified in the family Anacardiaceae. Trees in the genus *Pistacia*, most notably *Pistacia lentiscus* L., and in particular the cultivar *P. lentiscus* L. cv. Chia (cultivated on the Greek island of Chios), are known for their high yield of mastic. Other varieties include *P. lentiscus* L. var. *emarginate* Engl., and *P. lentiscus* L. var. *latifolia* Coss. Additional species of *Pistacia* include for example, *P. atlantica, P. palestina, P. saportae, P. terebinthus, P. vera* and *P. integerrima*.

As used herein, the terms "masticadienoic acid", "masticadienonic acid", "masticadienoic" and "masticadienonic" may interchangeably be used.

In order to provide clarity with respect to the molecular structure of compounds frequently mentioned and referred to in this application, a list of structures with names and acronyms used in this application is presented below.

Masticadienonic acid refers to 24-Z-masticadienonic acid, the acronym MDA used in the current application refers to this compound. The chemical structure of 24-Z-masticadienonic acid is as follows:

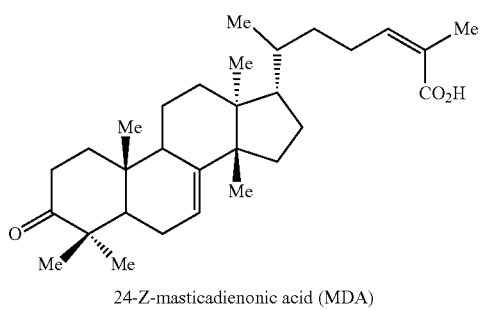

24-Z-masticadienonic acid (MDA)

Isomasticadienonic acid refers to 24-Z-isomasticadienonic acid, the acronym IMDA used in the current application refers to this compound. The chemical structure of 24-Z-isomasticadienonic acid is as follows:

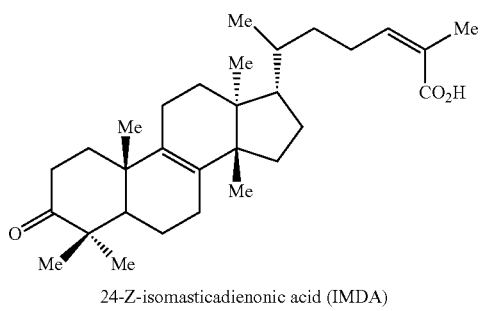

24-Z-isomasticadienonic acid (IMDA)

Oleanonic acid (OLN or OA) has the following molecular structure:

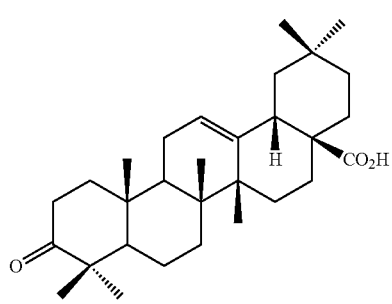

Oleanonic acid (OLN or OA)

Moronic acid (MO or MA) has the following molecular structure:

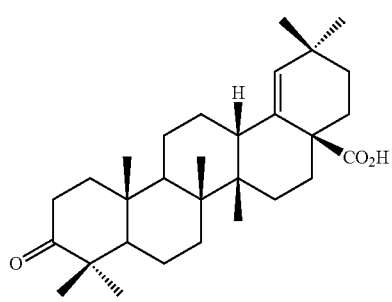

Moronic acid (MA)

24-Z-masticadienolic acid (MLA) has the following structure, the 3-hydroxyl group has the beta-configuration:

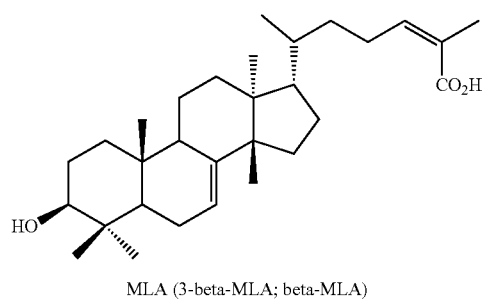

MLA (3-beta-MLA; beta-MLA)

24-Z-epimasticadienolic acid (epi-MLA) has the following structure, the 3-hydroxyl group has the alpha-configuration:

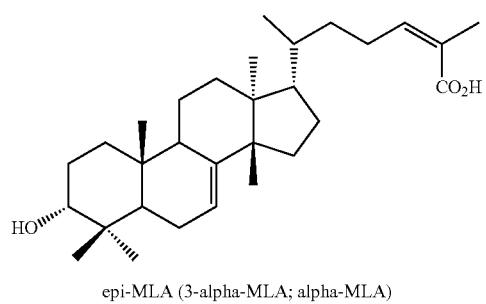

epi-MLA (3-alpha-MLA; alpha-MLA)

24-Z-isomasticadienolic acid (IMLA) has the following structure, the 3-hydroxyl group has the beta-configuration:

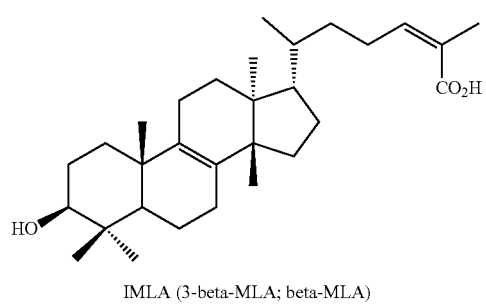

IMLA (3-beta-MLA; beta-MLA)

24-Z-epi-isomasticadienolic acid (epi-IMLA) has the following structure, the 3-hydroxyl group has the beta-configuration:

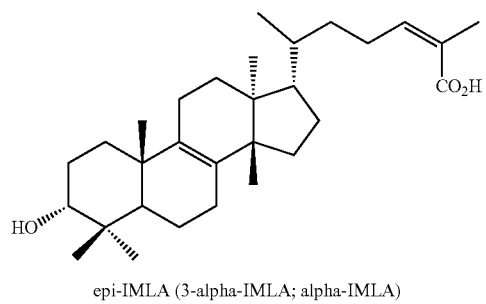

epi-IMLA (3-alpha-IMLA; alpha-IMLA)

24-Z-3-O-acetyl-masticadienolic acid has the following molecular structure:

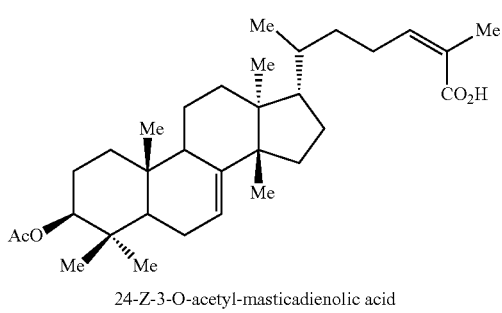

24-Z-3-O-acetyl-masticadienolic acid (3-O-acetyl-masticadienolic acid; 3-OAc-masticadienolic acid; 3-OAc-MLA)

24-Z-3-O-acetyl-epimasticadienolic acid has the following molecular structure:

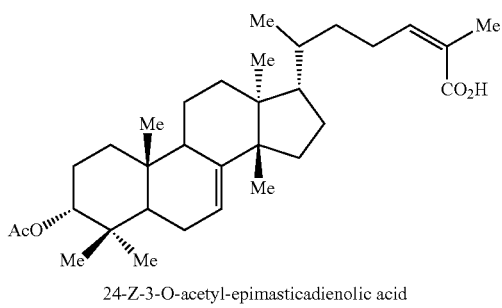

24-Z-3-O-acetyl-epimasticadienolic acid (3-O-acetyl-epimasticadienolic acid; 3-OAc-epimasticadienolic acid; 3-OAc-epi-MLA)

24-Z-3-O-acetyl-isomasticadienolic acid has the following molecular structure:

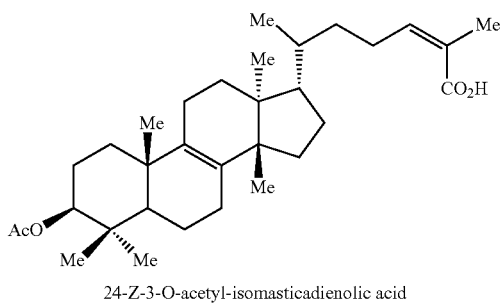

24-Z-3-O-acetyl-isomasticadienolic acid (3-O-acetyl-isomasticadienolic acid; 3-OAc-isomasticadienolic acid; 3-OAc-IMLA)

24-Z-3-O-acetyl-epiisomasticadienolic acid has the following molecular structure:

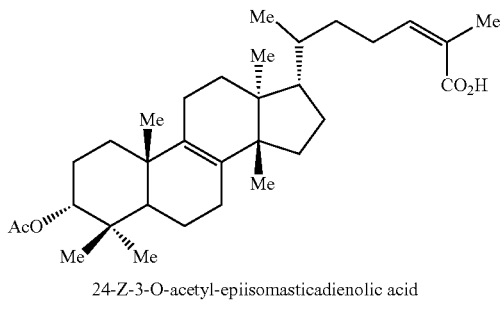

24-Z-3-O-acetyl-epiisomasticadienolic acid (3-O-acetyl-epiisomasticadienolic acid; 3-OAc-epiisomasticadienolic acid; 3-OAc-epi-IMLA)

As used herein, the term "isolated acidic fraction of mastic gum" refers to a fraction obtained following extraction of gum mastic with at least one polar and at least one non-polar organic solvent, followed by an acid-base extraction of a solution of the thus obtained material and isolation of the resulting acidic fraction. The isolated acidic fraction of the invention is soluble both in polar and non-polar organic solvents.

As used herein the term "plurality" refers to more than one, preferably more than two. As used herein the term "synergistic" means more than additive.

As used herein, the term "acid-base extraction" refers to a procedure in which an organic solvent solution containing organic acidic and organic non-acidic components is treated/extracted with one or more basic aqueous solution(s). As a result of this, the organic acidic components are deprotonated and thus converted into their corresponding ionic salt forms and as a result will dissolve in the said basic aqueous solution. The non-acidic organic components will stay behind in the original organic solution. Subsequently, the basic aqueous solution containing the salt forms of the acidic components is acidified, resulting in the reformation of the protonated acid forms of the organic acidic components. These protonated acid forms (acidic fraction) can be removed from the acidified aqueous solution in several ways depending on the properties of the acidic compounds. One option for removing the acidic fraction from the acidified solution is by extraction into a suitable organic solvent. Example 1 is a non-limiting example of an acid-base extraction as described above.

Depending on the solubility of the acidic compounds in the acidified aqueous solution, the acidic fraction may be isolated via filtration of the acidified aqueous solution.

Instead of using a basic aqueous solution for the acid-base extraction, basic forms of ion-exchange resins can be used as well. In these cases, the acidic organic components (acidic fraction) are captured in their deprotonated anionic form by the resin. The resin is subsequently removed from the initial solution, leaving non-acidic components behind. The acidic components (acidic fraction) are subsequently released from the resin by treatment of the resin with a suitable acidic solution.

The use of ion-exchange resins for acid-base extractions is especially suitable for process scale up and can be used for the development of (semi)continuous extraction processes.

Examples of the above acid-base extractions and other variations can be found in many textbooks and other publications, and are considered common knowledge to those skilled in the art. An example of a useful textbook is "Vogel's Textbook of Practical Organic Chemistry", 5$^{th}$ Edition, 1989, (p. 162-163).

As used herein, the term "degree of purity" refers to the content of a specified chemical compound in a preparation, expressed as a percentage on a weight per weight basis of the specified chemical compound relative to other chemical compounds in the preparation.

As used herein, "terpene compounds" refers to isoprene-containing hydrocarbons, having isoprene units ($CH_2$=C($CH_3$)—CH=$CH_2$) in a head-to-tail orientation. Terpene hydrocarbons in general, have the molecular formula ($C_5H_8$)$_n$, and include hemiterpenes, (C5), monoterpenes (C10), sesquiterpenes (C15), diterpenes (C20), triterpenes (C30), and tetraterpenes (C40) which respectively have 1, 2, 3, 4, 6 and 8 isoprene units. Terpenes may be further classified as acyclic or cyclic.

As used herein, "terpenoids" and "terpenoid compounds" interchangeably refer to terpene-related compounds which contain oxygen in addition to isoprene units, and thus include alcohols, aldehydes and ketones. Terpenoids are subdivided according to the number of carbon atoms in a manner similar to terpene and thus include hemiterpenoids, (C5), monoterpenoids (C10), sesquiterpenoids (C15), diterpenoids (C20), triterpenoids (C30), and tetraterpenoids (C40) which respectively have 1, 2, 3, 4, 6 and 8 isoprene units. The skeleton of terpenoids may differ from strict additivity of isoprene units by the loss or shift of a fragment, generally a methyl group. Examples of monoterpenoids include camphor, eugenol and borneol. Examples of diterpenoids include phytol and taxol. Examples of triterpenoids include squalene and lanosterol.

As used herein, "terpenoic acids" refer to terpenoid compounds containing at least one carboxylic acid group. The terpenoic acids may additionally contain one or more other oxygen-containing functional groups comprising hydroxyl, keto, aldehyde, ether (cyclic and non-cyclic) and ester (cyclic and non-cyclic) groups.

As used herein, "triterpenoic acids" refer to triterpenoid compounds containing at least one carboxylic acid group. The triterpenoic acids may additionally contain one or more other oxygen-containing functional groups comprising hydroxyl, keto, aldehyde, ether (cyclic and non-cyclic) and ester (cyclic and non-cyclic) groups.

As used herein, "an oligomeric form of a terpenoic acid" refers to an oligomeric terpenoid acid in which the monomeric units are either of the same terpenoic acid or of different terpenoic acids, and are joined in any possible arrangements, and are connected one to another through any possible bond or functional group, such as a C—C bond, an ester group or an ether group.

As used herein, "an oligomeric form of a triterpenoic acid" refers to an oligomeric triterpenoid acid in which the monomeric units are either of the same triterpenoic acid or of different triterpenoic acids, and are joined in any possible arrangements, and are connected one to another through any possible bond or functional group, such as a C—C bond, an ester group or an ether group.

As used herein, the terms "masticadienoic acid", "masticadienonic acid", "masticadienoic" and "masticadienonic acid" may interchangeably be used.

As used herein, the terms "isomasticadienoic acid", "isomasticadienonic acid", "isomasticadienoic" and "isomasticadienonic" may interchangeably be used.

As used herein, "substantially devoid" means that a preparation or pharmaceutical composition according to the invention that generally contains less than about 5% of the stated substance. For example, less than about 3%, less than 1%, less than 0.5%, less than 0.1%.

As used herein, the term "consisting essentially of" means that the only active pharmaceutical ingredient in the formulation or method that treats a specified condition is the specifically recited therapeutic ingredient in the particular embodiment. The presence of other ingredients, e.g., excipients and/or lubricants, etc., is not precluded. The presence of additional other pharmaceutically active agents is also not precluded, as long as the latter do not have actual effect on said condition.

As used herein, "therapeutically effective amount" refers to that amount of a pharmaceutical ingredient which substantially induces, promotes or results in a desired therapeutic effect.

As used herein, "pharmaceutically acceptable carrier" refers to a diluent or vehicle which is used to enhance the delivery and/or pharmacokinetic properties of a pharmaceutical ingredient with which it is formulated, but has no therapeutic effect of its own, nor does it induce or cause any undesirable or untoward effect or adverse reaction in the subject.

As used herein, "pharmaceutically acceptable hydrophobic carrier" refers to a hydrophobic non-polar diluent or vehicle in which a mastic fraction is dissolved or suspended.

As used herein, the terms "optic neuropathy" and "optic atrophy" may interchangeably be used. The terms refer to damage to the optic nerve due to any cause. The terms further encompass any condition or disorder resulting from or related to optic neuropathy, such as, ischemic optic neuropathy (including nonarteritic Anterior Ischemic Optic neuropathy (NAION), Anterior ischemic optic neuropathy (AION), Posterior ischemic optic neuropathy); Radiation optic neuropathy (RON)); Traumatic optic neuropathy, Glaucoma, Optic neuritis, Compressive optic neuropathy, Infiltrative optic neuropathy, Mitochondrial optic neuropathy, Nutritional optic neuropathies, toxic optic neuropathies, Hereditary optic neuropathy, damage resulting from storage disease, and the like; or combinations thereof. Each possibility is a separate embodiment.

As used herein, the term "storage disease" refers to any type of metabolic disorder that lead to excessive accumulation of substances such as lipids, proteins, lipoproteins, carbohydrates and others, of normal or abnormal nature. Of particular importance is the accumulation of lipofuscin associated with pathological damage to the optic nerve.

Numerical values stated herein are to be understood as the stated value +/−10%.

The term "about" is directed to include the stated value +/−10% of the stated value.

In some embodiments, the present invention provides compositions comprising specific combinations of terpenoic acids, such as that found in isolated acidic fractions of mastic gum. In some embodiments, the present invention provides compositions consisting of specific triterpenoic acids compounds, these compositions are shown to have an unexpected synergetic effect compared to the same individual triterpenoic acids compounds in the treatment of optic neuropathy. The triterpenoic acid compounds may be from a plant source, in particular mastic gum, or may be the products of chemical synthesis reactions. In some cases, the compositions may correspond to combinations of compounds, in which some are chemically synthesized and some are derived from plant sources.

In some embodiments, any one of the triterpenoic acids may be the product of a biochemical reaction or a product produced by a microbial organism. In some embodiments, any one of the triterpenoic acids may be the product of a fermentation process. In some embodiments, any one of the triterpenoic acids may be produced by a combination of a chemical synthesis and a biochemical reaction. In some embodiments, any one of the triterpenoic acids may be produced by a combination of a chemical synthesis and a fermentation process. In some embodiments, the any one of triterpenoic acids may be produced by a combination of any of the above-indicated options. In case of a biochemical reaction or microbial process, the biochemical agent and the microbial agent may be a naturally occurring agent or may be a modified agent not naturally occurring. Modification of these agents may have been achieved using modern biochemical methods such as for example genetic engineering. Said biochemical agents and microbial agents not occurring naturally may also have been created using synthetic biology methods.

In some embodiments, obtaining from a natural source may include isolating from a natural source. In some embodiments, the isolation from the natural source may include isolation as individual compound(s) or as a group(s) of compounds. In some embodiments, the natural source may include a plant material selected from the group consisting of a resin, a gum, leaves, twigs, roots, flowers, seeds, buds, bark, nuts and roots. Each possibility is a separate embodiment. In some embodiments, the natural source may include a resin extracted from at least one plant. In some embodiments, the natural source may include mastic gum.

In some embodiments, the natural source may include at least one plant. In some embodiments, the plant may be classified in the family Anacardiaceae. In some embodiments, the plant may comprise at least one plant classified in the genus/genera *Pistacia* and/or *Schinus*. In some embodiments, *Pistacia* may include species selected from the group consisting of *P. lentiscus, P. atlantica, P. palestina, P. saportae, P. terebinthus, P. vera P. integerrima*, and *P. lentiscus* L. Each possibility is a separate embodiment. In some embodiments, *Pistacia* may include the species *Pistacia lentiscus* L. In some embodiments, *Schinus* may include the species *S. molle*. In some embodiments, the *Pistacia* may include the species *Pistacia Lentiscus* var. Chia. In some embodiments, the *Pistacia* may include the species *Pistacia lentiscus* L. var. *latifolius* Coss. Each possibility is a separate embodiment of the invention.

Plant species useful for obtaining the compositions of the invention include without limitation, those of the genera *Pistacia, Pinus, Picea, Juniperus, Alsies, Larix, Ocimum, Laurus* and *Lavendula*.

Useful species of *Pistacia* include without limitation, *P. lentiscus, P. atlantica, P. palestina, P. saportae, P. terebinthus, P. vera* and *P. integerrima*.

The method used for obtaining isolated acidic fractions of mastic gum can be described as follows. By way of a general description, collected plant material, for example mastic gum, is combined in a suitable vessel with a suitable solvent, usually a polar solvent. Suitable polar solvents include for example, alcohols, ethers, esters, amides, aldehydes, ketones, nitriles and combinations thereof.

Particular examples of polar organic solvents are methanol, ethanol, propanol, isopropanol, 1-butanol, 2-butanol, sec-butanol, t-butanol, 1-pentanol, 2-pentanol, 3-pentanol, neopentanol, 3-methyl-1-butanol, 2-methyl-1-butanol, 3-methyl-2-butanol, 2-methyl-2-butanol, ethyleneglycol, ethyleneglycol monomethyl ether, diethyl ether, methylethyl ether, ethylpropyl ether, methylpropyl ether, 1,2-dimethoxyethane, tetrahydrofuran, dihydrofuran, furan, pyran, dihydropyran, tetrahydropyran, methyl acetate, ethyl acetate, propyl acetate, acetaldehyde, methylformate, ethylformate, ethyl propionate, methyl propionate, dichloromethane, chloroform, dimethylformamide, acetamide, dimethylacetamide, N-methylpyrrolidone, acetone, ethylmethyl ketone, diethyl ketone, acetonitrile, propionitrile, and combinations thereof.

The mastic gum and the solvent are preferably combined such that the solvent is in large excess, for example 10:1 or 20:1. The mixture may be periodically or continuously agitated over a period ranging from a few minutes to a number of hours. The solvent may be decanted without any treatment, or optionally the mixture may be first subjected to low speed centrifugation, for example at 100 to 2000 rpm, as is known in the art. The insoluble material is recovered from the extract and a fresh aliquot of solvent is added to the insoluble material, such that the extraction and dissolution process is repeated for a number of cycles, in order to obtain as much as possible of the polar solvent soluble compounds.

After the final dissolution step, the extracts containing polar solvent soluble material are combined and the polar solvent is evaporated (for example by using a rotary evaporation as is known in the art), so as to yield polar solvent soluble material, which may be referred to as a crude, or "first step" extract.

The first step extract material is combined with a non-polar organic solvent and extracted by shaking over a period of 1 to 2 hours. Suitable non-polar solvents include acyclic or cyclic, saturated or unsaturated aliphatic hydrocarbons and aromatic hydrocarbons, for example, C5-C10 alkanes, C5-C10 cycloalkanes, C6-C14 aromatic hydrocarbons, and combinations thereof. Each of the foregoing may be optionally substituted by one or more halogens, for example, C7-C14 perfluoroalkanes. Particular examples of non-polar organic solvents are pentanes, hexanes, heptanes, octanes, nonanes, decanes, cyclopentane, cyclohexane, cycloheptane, benzene, toluene, xylene, and isomers and mixtures thereof. Material remaining insoluble or precipitating in the presence of the non-polar solvent is removed and discarded. The non-polar solvent-soluble fraction is then obtained by evaporating the non-polar solvent (for example by rotary evaporation). This fraction may be referred to as purified or "two step" extract, corresponding to an isolated fraction of mastic gum which is characterized by the fact that it is soluble in both a polar solvent and a non-polar solvent, while materials which are soluble in the polar solvent but insoluble in the non-polar solvent, have been removed.

The second step extract material is subsequently dissolved in an organic solvent and this solution is extracted repeatedly (e.g. four times) with a basic aqueous solution. A second extraction with a different basic aqueous solution may be performed. The basic fraction thus obtained is acidified with a dilute aqueous acid solution to acidic pH. The acidified aqueous solution is extracted several times with an organic solvent. The thus obtained combined organic solvent extracts (also referred to as "three step extract") are treated with a drying agent. This isolated acidic fraction of mastic gum is then obtained by evaporating the organic solvent (for example by rotary evaporation). This fraction is referred to as the isolated acidic fraction of mastic gum. Additional intermediate steps of drying and/or solvent removal may be carried out between other steps, as is known in the art. Alternately, the second step extract material may be combined with a basic ion exchange resin e.g. Amberlyst® A26. The isolated ion-exchange resin is treated with an non-aqueous acidic solution in order to liberate the acidic fraction from the resin. The isolated acidic fraction is then obtained by evaporating the non-aqueous solvent and any excess acid.

The feature that distinguishes the isolated acidic fractions of the invention over prior art extracts of mastic gum is that certain acidic compounds have been removed in the first two steps of the procedure which would otherwise end up in the final acidic fraction. According to the teachings of the present invention, the acidic compounds removed during the first two steps of the isolation procedure have a detrimental effect on the beneficial biological activities of the isolated acidic fractions disclosed herein.

The three step extract may be dried further, for example by high vacuum treatment (for example <0.01 mbar for up to several days) to remove residual solvent and other volatile material, weighed and combined with a non-polar organic solvent or other carrier to effect its dissolution.

In some embodiments, the isolated fraction of the invention may be obtained by a process comprising one or more of the steps of:

(a) treating mastic gum with a polar organic solvent;
(b) isolating a fraction soluble in said polar organic solvent;
(c) optionally removing said polar organic solvent;
(d) treating the soluble fraction obtained in step (b) or (c) with a non-polar organic solvent,
(e) isolating a fraction soluble in said non-polar organic solvent;
(f) optionally removing said non-polar organic solvent;
(g) dissolving the fraction obtained in step (f) in an organic solvent;
(h) treating the solution obtained in step (g) with a basic solution so as to obtain a basic fraction; and
(i) acidifying the basic fraction obtained in step (h) with an acid solution.

In some embodiments, the treatment with a basic solution (basifying) in step (h) comprises extracting the solution obtained in step (g) with one or more suitable basic aqueous solution; or contacting the solution obtained in step (g) with a basic ion exchange resin. In case of a basic ion exchange resin, the resin may subsequently be treated with an acidic solution in order to release the captured acidic fraction. The isolated acidic fraction is than obtained by removal of any volatiles using, for example, application of vacuum.

In some embodiments, step (h) comprises contacting the solution obtained in step (g) with a basic ion exchange resin, and thereafter removing the basic ion exchange resin by filtration. The basic ion exchange resin may be subsequently treated with an acidic solution in order to liberate the captured acidic fraction. The isolated acidic fraction is than obtained by removal of any volatiles using e.g. application of vacuum.

In some embodiments, the process further comprises the steps of
(j) extracting the acidified fraction obtained in step (i) with an organic solvent;
k) optionally contacting the organic fraction obtained in step (j) with a drying agent so as to remove remaining water;
(l) removing organic solvent and/or excess acid from the fraction obtained in any of steps (i), (j) or (k); and
(m) dissolving the isolated fraction obtained in step (l) in a carrier.

The process may further comprise removing the solvent after any of steps (c), (f) or (l). Solvent removal may be carried out by any means known in the art, for example rotary evaporation, application of high vacuum and a combination thereof. In some embodiments, steps (a) to (c) are carried out prior to steps (d) to (f) or vice versa. In some embodiments, the polar organic solvent comprises ethanol, the non-polar organic solvent comprises hexane and the organic solvent used for the acid-base extraction comprises diethyl ether. As is readily understood by one of skill in the art, steps (a) to (c) and steps (d) to (f) may each be independently carried out for a number of cycles to optimize the extraction process and degree of purification of the product.

In some embodiments, step (h) comprises extracting the solution obtained in step (g) with a basic aqueous solution, and collecting the organic fraction obtained therefrom. In some embodiments, the process may further comprise combining the organic fraction obtained from step (h) with a fraction obtained in any of steps (i), (j) or (k).

In some embodiments, the organic fraction obtained in step (h) is combined with a fraction obtained in any of steps (i), (j) or (k) in an amount in the range from about 0.1 to 50% of the organic fraction obtained from step (h). In some embodiments, the amount is in the range from about 0.5-50%; or 2 to 25%; or 0.1 to 10%.

The isolated acidic fraction may comprise at least one terpenoic acid, such as a combination of various triterpenoic acid combinations. Triterpenoic acids include for example, masticadienonic acid; isomasticadienonic acid; isomasticadienolic acid; 3-O-acetyl-masticadienolic acid; 3-O-acetyl-epi-masticadienolic acid; 3-O-acetyl-isomasticadienolic acid, 3-O-acetyl-epi-isomasticadienolic acid; masticadienolic acid, oleanonic acid; oleanolic acid; ursonic acid; ursolic acid; moronic acid; and 3-oxo-lup-20(29)-en-28-oic acid.

The isolated acidic fraction may comprise at least one terpenoic acid, such as a combination of various triterpenoic acid combinations. Triterpenoic acids include for example, masticadienonic acid; isomasticadienonic acid; masticadienolic acid; isomasticadienolic acid; 3-O-acetyl-masticadienolic acid; 3-O-acetyl-epi-masticadienolic acid; 3-O-acetyl-isomasticadienolic acid, 3-O-acetyl-epi-isomasticadienolic acid; oleanonic acid; oleanolic acid; ursonic acid; ursolic acid; moronic acid; and 3-oxo-lup-20(29)-en-28-oic acid.

In some embodiments, the isolated acidic fraction may comprise at least two terpenoic acid compounds, selected from, for example, masticadienonic acid; isomasticadienonic acid; masticadienolic acid; isomasticadienolic acid; 3-O-acetyl-masticadienolic acid; 3-O-acetyl-epimasticadienolic acid; 3-O-acetyl-isomasticadienolic acid, 3-O-acetyl-epi-isomasticadienolic acid; oleanonic acid; oleanolic acid; ursonic acid; ursolic acid; moronic acid; and 3-oxo-lup-20(29)-en-28-oic acid.

In some embodiments, the isolated acidic fraction may comprise at least two terpenoic acid compounds, selected from, for example, masticadienonic acid; isomasticadienonic acid; isomasticadienolic acid; 3-O-acetyl-masticadienolic acid; 3-O-acetyl-epimasticadienolic acid; 3-O-acetyl-isomasticadienolic acid, 3-O-acetyl-epi-isomasticadienolic acid; oleanonic acid; oleanolic acid; ursonic acid; ursolic acid; moronic acid.

In some embodiments, the isolated acidic fraction may comprise at least two terpenoic acid compounds, selected from, for example, masticadienonic acid; isomasticadienonic acid; masticadienolic acid, isomasticadienolic acid; 3-O-acetyl-masticadienolic acid; 3-O-acetyl-epimasticadienolic acid; 3-O-acetyl-isomasticadienolic acid, 3-O-acetyl-epi-isomasticadienolic acid; oleanonic acid; oleanolic acid; ursonic acid; ursolic acid; moronic acid; and 3-oxo-lup-20(29)-en-28-oic acid.

In some embodiments, the isolated acidic fraction may comprise at least two terpenoic acid compounds, selected from, for example, masticadienonic acid; isomasticadienonic acid; masticadienolic acid, isomasticadienolic acid; 3-O-acetyl-masticadienolic acid; 3-O-acetyl-epimasticadienolic acid; 3-O-acetyl-isomasticadienolic acid, 3-O-acetyl-epi-isomasticadienolic acid; oleanonic acid; oleanolic acid; ursonic acid; ursolic acid; moronic acid.

In some embodiments, the isolated acidic fraction may comprise at least three terpenoic acid compounds, selected from, masticadienonic acid; isomasticadienonic acid; isomasticadienolic acid; 3-O-acetyl-masticadienolic acid; 3-O-acetyl-epimasticadienolic acid; 3-O-acetyl-isomasticadienolic acid, 3-O-acetyl-epi-isomasticadienolic acid; oleanonic acid; oleanolic acid; ursonic acid; ursolic acid; moronic acid; and 3-oxo-lup-20(29)-en-28-oic acid.

In some embodiments, the isolated acidic fraction may comprise at least two terpenoic acid compounds, selected from, masticadienonic acid, isomasticadienonic acid, and oleanonic acid.

In some embodiments, the isolated acidic fraction may be substantially devoid of particular triterpenoic acids, such as, for example, masticadienolic acid or moronic acid. Each possibility is a separate embodiment.

In some embodiments, the isolated acidic fraction may be substantially devoid of essential oils.

Furthermore, terpenoic acid and or triterpenoic acids in the isolated acidic fraction may be in monomeric form, or in an oligomeric form, such as a dimer, a trimer, or combinations thereof.

The composition for use in the invention comprises a therapeutically effective amount of an isolated acidic fraction of mastic gum described herein, and a pharmaceutically acceptable hydrophobic carrier.

The invention also provides a composition comprising at least one triterpenoic acid; and a pharmaceutically acceptable carrier. The triterpenoic acid may be isolated from a plant product, such as mastic gum, as hereinbefore described, or it may be the product of a chemical synthesis. Furthermore, the composition may comprise a combination of triterpenoic acids, some of which are chemically synthesized, and some of which are isolated from one or more plant products. In some embodiments, the composition may consist of at least two triterpenoic acids compounds as the pharmaceutically active ingredients, and a pharmaceutically acceptable carrier. In addition, the composition may comprise dimeric, trimeric and higher oligomeric forms of triterpenoic acids; the oligomers can be formed from both identical and different monomeric triterpenoic acids. In some embodiments, the composition may consist of at least three triterpenoic acids compounds as the pharmaceutically active ingredients, and a pharmaceutically acceptable carrier.

For preparation of a composition for therapeutic use, suitable carriers may be used, such as hydrophobic carriers including pharmaceutically acceptable oils, optionally in combination with waxes, as described herein.

An hydrophobic carrier comprises at least one oil, such as for example a mineral oil, a vegetable oil or combinations thereof.

The term "mineral oil" refers to a clear colorless nearly odorless and tasteless liquid obtained from the distillation of petroleum. It may also be referred to as white oil, white mineral oil, liquid petrolatum, liquid paraffin or white paraffin oil. In accordance with some embodiments of the invention, the mineral oil is light mineral oil, a commercially available product which may be obtained either as a NF (National Formulary) grade product or as a USP (US Pharmacopoeia) grade product. For use in the invention, the mineral oil is preferably free of aromatics and unsaturated compounds.

Suitable vegetable oils include, but are not limited to cottonseed oil, olive oil, almond oil, canola oil, coconut oil, corn oil, grape seed oil, peanut oil, saffron oil, sesame oil, soybean oil, or combinations thereof. In some embodiments, the mineral oil is light mineral oil.

The pharmaceutically acceptable carrier may alternately or in addition comprise an oil replacement. Oil replacements include alkanes having at least 10 carbon (e.g., isohexadecane), benzoate esters, aliphatic esters, noncomodogenic esters, volatile silicone compounds (e.g., cyclomethicone), and volatile silicone substitutes. Examples of benzoate esters include $C_{12}C_{15}$ alkyl benzoate, isostearyl benzoate, 2-ethyl hexyl benzoate, dipropylene glycol benzoate, octyldodecyl benzoate, stearyl benzoate, and behenyl benzoate. Examples of aliphatic esters include $C_{12}C_{15}$ alkyl octonoate and dioctyl maleate. Examples of noncomodogenic esters include isononyl isononanoate, isodecyl isononanoate, diisostearyl dimer dilinoleate, arachidyl propionate, and isotridecyl isononanoate. Examples of volatile silicone substitutes include isohexyl decanoate, octyl isononanoate, isononyl octanoate, and diethylene glycol dioctanoate.

Cyclomethicone is an evaporative silicone which may be included in the carrier to assist in making the composition amenable to ejection from a spray dispenser. Furthermore, due to its evaporative property, cyclomethicone may assist in retaining and fixing the formulation on the surface to which it is sprayed e.g. a wound site.

The hydrophobic carrier may further comprise at least one wax. Waxes include for example, beeswax; vegetable waxes, sugar cane waxes, mineral waxes, and synthetic waxes. Vegetable waxes include for example, carnauba, candelilla, ouricury and jojoba wax. Mineral waxes include for example, paraffin wax, lignite wax, microcrystalline waxes and ozokerites. Synthetic waxes include for example, polyethylene waxes.

The pharmaceutical composition may be formulated in any of a number of forms such as for example, a capsule (including a softgel capsule), a tablet, a gel, a liposome, a suppository, a suspension, an ointment, a solution, an emulsion or microemulsion, a film, a cement, a powder, a glue, an aerosol, a spray and a gel.

For preparing the pharmaceutical composition, the isolated acidic fraction of mastic gum may be suitably formulated as inclusion complexes, nanoemulsions, microemulsions, powders and liposomes. In some embodiments, an inclusion complex comprises at least one cyclodextrin. In some embodiments, cyclodextrins comprise hydroxypropyl-β-cyclodextrin. In some embodiments, nanoemulsions comprise droplets having average particle size of less than 800 nm. In some embodiments, the droplets have average particle size of less than 500 nm. In some embodiments, the droplets have average particle size of less than 200 nm. In some embodiments, powders are spray dried powders. In some embodiments, liposomes comprise multilamellar vesicles. In some embodiments, a microemulsion comprises a non-ionic surfactant. Non-ionic surfactants include, without limitation, polyoxyl castor oils, polyoxyethylene sorbitan fatty acid esters (polysorbates), a poloxamer, a vitamin E derivative, polyoxyethylene alkyl ethers, polyoxyethylene sterates, saturated polyglycolyzed glycerides or combinations thereof.

According to some embodiments, various formulations of isolated acidic fraction and preparation thereof are disclosed herein in Example 1. The pharmaceutical compositions of the invention may be administered by any means that achieve their intended purpose. In some embodiments, administration is by parenteral route. In some embodiments, administration is a parenteral, localized administration. In some embodiments, parenteral administration may be selected from, but not limited to: intravenous, intramuscular, subcutaneous, intradermal, intraperitoneal, intraarterial, intrauterine, intraurethral, intracardial, intracerebral, intracerebroventricular, intrarenal, intrahepatic, intratendon, intraosseous, intraocular, and intrathecal routes of administration.

The dosage administered will be dependent upon the age, health, and weight of the subject, the use of concurrent treatment, if any, frequency of treatment, and the nature of the effect desired. The amount of the isolated acidic fraction of mastic gum of the present invention in any unit dosage form comprises a therapeutically effective amount which may vary depending on the recipient subject, route and frequency of administration.

The amount of the isolated acidic fraction of mastic gum present in the pharmaceutical composition may be in the range from about 0.01% to about 99%. In general, the amount of the isolated acidic fraction of mastic gum present in the pharmaceutical composition may conveniently be in the range from about 0.01% to about 50%, such as, 0.01% to about 25%, such as 0.01% to about 12%, on a weight per weight basis, based on the total weight of the composition. For topical use, the percentage of the isolated acidic fraction of mastic gum in the composition may be in the range from about 0.05% to about 2.5%. For administration by injection, the percentage of the isolated acidic fraction of mastic gum in the composition may be conveniently in the range from about 0.1% to about 7%.

In some embodiments, the triterpenoic acids may comprise from about 1% to about 80% of the total active ingredients of the composition. In some embodiments, the triterpenoic acids may comprise up to 99% of the total active ingredients of the composition. In some embodiments, the triterpenoic acids may comprise from about 10% to about 80% of the total active ingredients of the composition. In some embodiments, the triterpenoic acids may comprise from about 20% to about 80% of the total active ingredients of the composition. In some embodiments, the triterpenoic acids may comprise from about 30% to about 70% of the total active ingredients of the composition. In some embodiments, the triterpenoic acids may comprise from about 35% to about 65% of the total active ingredients of the composition. In some embodiments, the triterpenoic acids may comprise from about 40% to about 60% of the total active ingredients of the composition.

In some embodiments, the triterpenoic acids may comprise from about 0.01% to about 80% of the total composition. In some embodiments, the triterpenoic acids may comprise from about 0.01% to about 50% of the total composition. In some embodiments, the triterpenoic acids may comprise from about 0.01% to about 10% of the total composition. In some embodiments, the triterpenoic acids may comprise from about 0.1% to about 10% of the total composition. In some embodiments, the triterpenoic acids may comprise from about 0.5% to about 4% of the total composition. In some embodiments, the triterpenoic acids may comprise from about 0.1% to about 0.5% of the total composition. In some embodiments, the triterpenoic acids may comprise from about 0.1% to about 1.0% of the total composition. In some embodiments, the triterpenoic acids may comprise from about 0.1% to about 2% of the total composition. In some embodiments, the triterpenoic acids may comprise from about 1% to about 3.5% of the total composition. In some embodiments, the triterpenoic acids may comprise from about 1.5% to about 3% of the total composition. In some embodiments, the triterpenoic acids may comprise from about 1.75% to about 2.75% of the total composition. In some embodiments, the triterpenoic acids may comprise from about 2% to about 2.5% of the total composition.

In some embodiments, the combination of triterpenoic acids may include as the main compounds one or more of: Moronic acid, Oleanonic acid, 24-Z-Masticadienonic acid, 24-Z-Isomasticadienonic acid, 24-Z-3-beta-OAc-masticadienolic acid, and/or 24-Z-3-beta-OAc-isomasticadienolic acid. Each possibility is a separate embodiment.

In some embodiments, the combination of triterpenoic acids may include as the main compounds: Moronic acid (12-15%), Oleanonic acid (18-20%), 24-Z-Masticadienonic acid (20-22%), 24-Z-Isomasticadienonic acid (22-26%), 24-Z-3-beta-OAc-masticadienolic acid (4-7%), and/or 24-Z-3-beta-OAc-isomasticadienolic acid (4-7%). Each possibility is a separate embodiment.

In some embodiments, these combinations of triterpenoic acids may further include (in addition to the main compounds) additional other triterpenoic acids in small amounts, typically less than 5%. Such additional possible other triterpenoic acids may be selected from one or more of: MLA: 3-beta-masticadienolic acid, IMLA: 3-beta-isomasticadienolic acid, 3-beta-OAc-epimasticadienolic acid, 3-beta-OAc-epi-isomasticadienolic acid, Epimasticadienolic acid (3-alpha-masticadienolic acid), Epi-isomasticadienolic acid (3-alpha-isomasticadienolic acid), Dihydromasticadienonic acid and/or Dihydroisomasticadienonic acid. Each possibility is a separate embodiment.

In some embodiments, the triterpenoic acids in an isolated acidic fraction of mastic gum may include as the main compounds one or more of: Moronic acid, Oleanonic acid, 24-Z-Masticadienonic acid, 24-Z-Isomasticadienonic acid, 24-Z-3-beta-OAc-masticadienolic acid, and/or 24-Z-3-beta-OAc-isomasticadienolic acid. Each possibility is a separate embodiment.

In some embodiments, the triterpenoic acids in an isolated acidic fraction of mastic gum may include as the main compounds: Moronic acid (12-15%), Oleanonic acid (18-20%), 24-Z-Masticadienonic acid (20-22%), 24-Z-Isomasticadienonic acid (22-26%), 24-Z-3-beta-OAc-masticadienolic acid (4-7%), and/or 24-Z-3-beta-OAc-isomasticadienolic acid (4-7%). Each possibility is a separate embodiment.

In some embodiments, these triterpenoic acids in an isolated acidic fraction of mastic gum may further include (in addition to the main compounds) additional other triterpenoic acids in small amounts, typically less than 5%. Such additional possible other triterpenoic acids may be selected from one or more of: MLA: 3-beta-masticadienolic acid, IMLA: 3-beta-isomasticadienolic acid, 3-beta-OAc-epimasticadienolic acid, 3-beta-OAc-epi-isomasticadienolic acid, Epimasticadienolic acid (3-alpha-masticadienolic acid), Epi-isomasticadienolic acid (3-alpha-isomasticadienolic acid), Dihydromasticadienonic acid and/or Dihydroisomasticadienonic acid. Each possibility is a separate embodiment.

In some embodiments, the amount of masticadienonic acid and isomasticadienonic acid in compositions consisting of these two compounds as the active ingredients may be in the range of about 0.05% to about 45% for each compound. In exemplary embodiments, the amounts of masticadienonic acid and isomasticadienonic acid in compositions consisting of these two compounds as the active ingredients may be in the range of about 0.05% to about 20% for each compound. For administration by injection, the amount for each may be in the range from about 0.1% to about 10%. For topical administration, the amount for each may be in the range from about 0.5% to about 12%. For oral administration, the amount for each may be in the range from about 0.5% to about 15%.

In some embodiments, the amount of oleanonic acid, masticadienonic acid and isomasticadienonic acid in compositions consisting of these three compounds as the active ingredients may be in the range of about 0.05% to about 30% for each compound. In exemplary embodiments, the amount of oleanonic acid, masticadienonic acid and isomasticadienonic acid in compositions consisting of these three compounds as the active ingredients may be in the range of about 0.05% to about 15% for each compound. For administration by injection, the amount for each may be in the range from about 0.1% to about 10%. For topical administration, the amount for each may be in the range from about 0.5% to about 12%. For oral administration, the amount for each may be in the range from about 0.5% to about 15%.

The pharmaceutical compositions of the invention may be manufactured in a manner which is itself known to one skilled in the art, for example, by means of conventional mixing, granulating, dragee-making, softgel encapsulation, dissolving, extracting, or lyophilizing processes. Pharmaceutical compositions for oral use may be obtained by combining the active compounds with solid and semi-solid excipients and suitable preservatives, and/or antioxidants. Optionally, the resulting mixture may be ground and processed. The resulting mixture of granules may be used, after adding suitable auxiliaries, if necessary, to obtain tablets, softgels, capsules, or dragee cores.

Suitable excipients are, in particular, fillers such as saccharides, e.g., lactose or sucrose, mannitol or sorbitol; cellulose preparations and/or calcium phosphates, e.g., tricalcium phosphate or calcium hydrogen phosphate; as well as binders, such as starch paste, using, e.g., maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are flow-regulating agents and lubricants, e.g., silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxypropylmethyl-cellulose phthalate, are used. Dye stuffs or pigments may be added to the tablets or dragee coatings, e.g., for identification or in order to characterize combinations of active compound doses.

Formulations for parenteral administration include suspensions and microparticle dispersions of the active compounds as appropriate. In some embodiments, oily injection suspensions may be administered. Suitable lipophilic solvents or vehicles include fatty oils, e.g., sesame oil, or synthetic fatty acid esters, e.g., ethyl oleate, triglycerides, polyethylene glycol-400, cremophor, or cyclodextrins. Injection suspensions may contain substances which increase the viscosity of the suspension include, e.g., sodium carboxymethyl cellulose, sorbitol, and/or dextran. Optionally, the suspension may also contain stabilizers.

Pharmaceutical compositions can also be prepared using liposomes comprising the active ingredient. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolisable lipid capable of forming liposomes can be used. In general, the preferred lipids are phospholipids and the phosphatidyl cholines (lecithins), both natural and synthetic. Methods to form liposomes are known in the art, as disclosed for example, in Prescott, Ed., Methods in Cell Biology, Volume XIV, Academic Press, New York, N.Y. (1976).

The pharmaceutical composition may comprise an oil-in-water emulsion or microemulsion in order to facilitate its formulation for parenteral use Such emulsions/microemulsions generally include lipids, surfactants, optionally humectants, and water. Suitable lipids include those generally known to be useful for creating oil-in-water emulsions/microemulsions, for example fatty acid glyceride esters. Suitable surfactants include those generally known to be useful for creating oil-in-water emulsions/microemulsions wherein lipids are used as the oil component in the emulsion. Non-ionic surfactants may be preferred, such as for example, ethoxylated castor oil, phospholipids, and block copolymers of ethylene oxide and propylene oxide. Suitable humectants, if used, include for example propylene glycol or polyethylene glycol.

The pharmaceutical composition may be formulated in the form of a gel, such as a hydrogel formed from a gel-forming polymer such as carrageenan, xanthan gum, gum karaya, gum acacia, locust bean gum, guar gum. A hydrogel may be combined with an oil-in-water emulsion comprising the active ingredient.

The pharmaceutical composition may be formulated in the form of a cement such as those comprising polymethylmethacrylate (PMMA) or calcium phosphate, as are used in orthopedic surgery.

The pharmaceutical composition may be formulated in the form of a powder.

According to some embodiments, there are provided therapeutic uses and methods of treating optic neuropathy. The methods comprise administering to the subject a therapeutically effective amount of a composition comprising an isolated acidic fraction of mastic gum, or combination of isolated acidic compounds, as described herein. In some embodiments, the methods comprise administering to the subject a therapeutically effective amount of a composition comprising an isolated acidic fraction of mastic gum, as described herein. In some embodiments, the method comprises administering to the subject a therapeutically effective amount of a composition comprising a combination of at least two triterpenoic acids selected from: masticadienonic acid; isomasticadienonic acid; isomasticadienolic acid; 3-O-acetyl-masticadienolic acid; 3-O-acetyl-epimasticadienolic acid; 3-O-acetyl-isomasticadienolic acid, 3-O-acetyl-epi-isomasticadienolic acid; oleanonic acid, and moronic acid. In some embodiments, the method comprises administering to the subject a therapeutically effective amount of a composition comprising a combination of at least two triterpenoic acids selected from: masticadienonic acid; isomasticadienonic acid; 3-O-acetyl-masticadienolic acid; 3-O-acetyl-isomasticadienolic acid; oleanonic acid; and moronic acid. In some embodiments, the method comprises administering to the subject a therapeutically effective amount of a composition comprising a combination of at least two triterpenoic acids selected from: masticadienonic acid; isomasticadienonic acid; masticadienolic acid; isomasticadienolic acid; 3-O-acetyl-masticadienolic acid; 3-O-acetyl-isomasticadienolic acid; oleanonic acid; and moronic acid. In further embodiments, the method comprise administering to the subject a therapeutically effective amount of a composition comprising a combination of at least two triterpenoic acids selected from masticadienonic acid; isomasticadienonic acid and oleanonic acid. In some embodiments, the method comprises administering to the subject a therapeutically effective amount of a composition comprising triterpenoic acids consisting of masticadienonic acid and isomasticadienonic acid. In further exemplary embodiments, the method comprises administering to the subject a therapeutically effective amount of a composition comprising triterpenoic acids consisting of oleanonic acid, masticadienonic acid and isomasticadienonic acid.

In some embodiments, the step of administering the compositions may comprise any acceptable route including parenteral route. Parenteral administration includes, for example, intravenous, intramuscular, subcutaneous, intradermal, intraperitoneal, intraarterial, intrauterine, intraurethral, intracardial, intracerebral, intracerebroventricular, intrarenal, intrahepatic, intratendon, intraosseous. intraocular and intrathecal routes of administration. Each possibility is a separate embodiment.

In some embodiments, the compositions disclosed herein may be administered by any suitable administration route on any suitable administration regime at any suitable dose, depending on the subject characteristics (including, for example, age, gender, treated condition, severity of the condition, and the like). For example, administration may be performed 1-7 times a week. For example, administration may be performed more than once a day. For example, the compositions may be administered on a twice weekly schedule with even intervals. In some embodiments, the compositions may be administered on a schedule of every second day. In some embodiments, the compositions may be administered on a schedule of once every seventh day (once weekly). In some embodiments, the compositions may be administered once a day.

In some embodiments, the composition may be administered on a twice weekly schedule with even intervals. In some embodiments, the composition may be administered on a schedule of every second day. In some embodiments, the composition may be administered on a schedule of once every seventh day (once weekly). In some embodiments, the composition may be administered once a day.

In some embodiments, the composition may be administered as a 5% (w/w) formulation of the isolated acidic fraction of mastic gum or combinations of triterpenoic acids in cottonseed oil. In some embodiments, the composition may be administered as a 5% (w/w) formulation of the isolated acidic fraction of mastic gum or combinations of triterpenoic acids in stabilized cottonseed oil.

In some embodiments, the composition may be administered as a 5% (w/w) formulation of the isolated acidic fraction of mastic gum or combinations of triterpenoic acids in BHT-stabilized cottonseed oil. In some embodiments, the composition may be administered as a 5% (w/w) formulation of the isolated acidic fraction of mastic gum or combinations of triterpenoic acids in cottonseed oil, twice weekly schedule with even intervals. In some embodiments, the composition may be administered as a 5% (w/w) formulation of the isolated acidic fraction of mastic gum or combinations of triterpenoic acids in cottonseed oil, on a once a week schedule with even intervals (every seventh day). In some embodiments, the composition may be administered as a 5% (w/w) formulation of the isolated acidic fraction of mastic gum or combinations of triterpenoic acids in cottonseed oil, on a once daily schedule with even intervals.

In some embodiments, the composition may be administered in a dose of 0.4 milliliter (ML) of a 5% (w/w) formulation of the isolated acidic fraction of mastic gum or combinations of triterpenoic acids. In some embodiments, the composition may be administered in a dose of 0.2 milliliter (ML) of a 5% (w/w) formulation. In some embodiments, the composition may be administered in a dose of 0.8 milliliter (ML) of a 5% (w/w) formulation. In some embodiments, the composition may be administered in a dose of 0.4 milliliter (ML) as a 5% (w/w) formulation of the isolated acidic fraction of mastic gum or combinations of triterpenoic acids in cottonseed oil, twice weekly with even intervals. In some embodiments, the composition may be administered in a dose of 0.2 milliliter (ML) as a 5% (w/w) formulation of the isolated acidic fraction of mastic gum or combinations of triterpenoic acids in cottonseed oil, twice weekly with even intervals. In some embodiments, the composition may be administered in a dose of 0.8 milliliter (ML) as a 5% (w/w) formulation of the isolated acidic fraction of mastic gum or combinations of triterpenoic acids in cottonseed oil, twice weekly with even intervals.

It is clear to a person skilled in the art that many variations of the above-indicated administration routes, schedules, doses and regimens can be envisaged and designed. It is to be understood that such variations in administration routes, schedules, doses and regimens are also within the scope of the current invention.

According to some embodiments, the methods disclosed herein for treating optic neuropathy are particularly advantageous for subjects afflicted with conditions resulting from or associated with damage to the optical nerve, such as, for example, glaucoma, Traumatic Neuropathy, Ischemic optic neuropathy (such as, for example, NAION and AION), Glaucoma, Neuropathy caused by tumors, Neuropathy caused by infections, Mitochondrial optic neuropathies, Nutritional optic neuropathies, Radiation optic neuropathy, Toxic optic neuropathy, Retinal diabetic complications, damage caused by deposition disease, and the like, or combinations thereof.

In some embodiments, the uses and methods disclosed herein for treating optic neuropathy are particularly advantageous for subjects afflicted with conditions resulting from or associated with damage to the optical nerve as a result of a deposition disease, such as, deposition of lipoproteinaceous substances in the optic nerve, deposition of lipofuscin.

In some embodiments, the uses and methods disclosed herein for treating optic neuropathy are particularly advantageous for subjects afflicted with conditions resulting from or associated with deposition of lipoproteinaceous substances in the optic nerve.

In some embodiments, the uses and methods disclosed herein for treating optic neuropathy are particularly advantageous for subjects afflicted with conditions resulting from or associated with damage to the optical nerve as a result of deposition of lipoproteinaceous substances in the optic nerve, wherein the deposition of lipoproteinaceous substances is the result of a storage disease.

In some embodiments, the uses and methods disclosed herein for treating optic neuropathy are particularly advantageous for subjects afflicted with conditions resulting from or associated with damage to the optical nerve as a result of deposition of lipoproteinaceous substances in the optic nerve, wherein the deposition of lipoproteinaceous substances is the result of a storage disease, and wherein the deposited lipoproteinaceous substance is lipofuscin.

In some embodiments, the uses and methods disclosed herein for treating optic neuropathy are particularly advantageous for subjects afflicted with conditions resulting from or associated with damage to the optical nerve as a result of deposition of mineral substances in the optic nerve, wherein the deposition of mineral substances is the result of a storage disease, and wherein the mineral substances deposited in the optic nerve contain calcium and/or iron.

In some embodiments, the uses and methods disclosed herein for treating optic neuropathy are particularly advantageous for subjects afflicted with Glaucoma.

In some embodiments, the uses and methods of treatment disclosed herein are suitable for application in humans and non-human mammals.

According to some embodiments, the methods of the invention may encompass use of an article of manufacture which incorporates the composition comprising isolated acidic fraction of mastic gum, as described herein.

In some embodiments, the pharmaceutical composition may be in the form of a coating on the article of manufacture, or may be contained within a vessel which is integral to the article of manufacture.

In some embodiments, the pharmaceutical composition may be incorporated to a delivery device such as a needle, an injection device or a spray dispenser from which the composition is delivered to a body site requiring the therapy.

In some embodiments, articles of manufacture include, but are not limited to a needle, a microneedle, an injection device and a spray dispenser.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1A: Preparation of the Isolated Acidic Fraction of Mastic Gum

To a 50 gram amount of mastic gum was added absolute ethanol (800 ML) and the mixture was left to stand for 24 hours. The mixture was shaken for 30 minutes at 150 rpm and left to stand for two hours. The obtained ethanol solution was decanted from insoluble material into a 3 L round bottom flask. To the insoluble material was added 400 ML of fresh ethanol and the mixture was shaken again 30 minutes at 150 rpm and was left to stand for 30 minutes. The obtained ethanol solution was decanted and added to the first ethanol solution. This step was repeated once more using 200 ML absolute ethanol. This gave 1.4 L of ethanol solution. The ethanol was evaporated using a rotary evaporator, and to the remaining material was added n-hexane (1.2 Liter) and the mixture was shaken at 150 rpm for 4 hours. It was then left to stand for 4 hours and the hexane solution was decanted from insoluble material into a 3 L Erlenmeyer. To the remaining insoluble material was added 800 ML fresh hexane and the mixture was shaken for 6 hours at 150 rpm and left to stand for 12 hours. The hexane solution was decanted into the 3 L Erlenmeyer flask containing the first 1.2 L of hexane solution. The hexane was evaporated in a clean 3 L round bottom flask to give about 30 grams of extract. (Yields range typically from 50-70% depending on the age and particle size of the used Mastic gum.)

The obtained extracted material was subsequently dissolved in diethyl ether (500 ML) and extracted with a 5% aqueous sodium carbonate solution (4×100 ML), the basic aqueous layer and an oily/emulsion layer were carefully separated from the diethyl ether layer. The diethyl ether layer was then additionally extracted with 0.4 N aqueous sodium hydroxide (3×100 ML) and the basic aqueous layer and an oily/emulsion layer were again carefully separated from the diethyl ether layer. The two basic aqueous extracts (including oily/emulsion layers) were separately acidified to pH 1-2 by slow addition of 10% aqueous hydrochloric acid and were subsequently extracted with fresh diethyl ether (3×200 ML). The thus obtained etheral fractions were combined and dried over anhydrous sodium sulfate. After filtering off the sodium sulfate, the diethyl ether was removed using a rotary evaporator. This procedure gave ca. 15 gram of isolated acidic fraction of mastic gum as a white solid, corresponding to about 50% yield based on the intermediate extract obtained after the ethanol/hexane extraction. This particular isolated acidic fraction is termed herein "Acidic Mixture 1" or "Acidic-1".

Based on the starting 50 grams of Mastic gum, the yield for this acidic fraction is about 30%. Typical yields of this particular acidic fraction from mastic gum range from about 25% to about 35%. Without wishing to be bound to any theory or mechanism, these variations in yield can occur due to natural (e.g. seasonal) fluctuations in the composition of the Mastic gum and may also be influenced by age and storage conditions of the Mastic gum.

Example 1B

A further isolated acidic fraction of mastic gum was prepared according to the same method as Example 1A, but using methanol instead of ethanol as the polar solvent. Hexane was used as the non-polar solvent, and diethyl ether as the solvent for the acid-base extraction step.

Example 1C

A further isolated acidic fraction of mastic gum was prepared according to the same method as Example 1A, but using isopropanol as polar solvent. Hexane was used as the non-polar solvent, and diethyl ether as the solvent for the acid-base extraction step.

Example 1D

A further isolated acidic fraction of mastic gum was prepared according to the same method as Example 1A, but using n-heptane instead of hexane as the non-polar solvent. Ethanol was used as the polar solvent and diethyl ether as the solvent for the acid-base extraction.

Example 1E

A further isolated acidic fraction of mastic gum was prepared according to the same method as Example 1A, but using n-heptane instead of hexane as the non-polar solvent. Methanol was used as the polar solvent and diethyl ether as the solvent for the acid-base extraction.

Example 1F

A further isolated acidic fraction of mastic gum was prepared according to the same method as Example 1A, but using hexane as the non-polar solvent. Ethanol was used as the polar solvent and methyl-tert-butyl ether (MTBE) as the solvent for the acid-base extraction.

Example G—Isolated Acidic Fraction and Neutral Fraction of Mastic Gum Using Ion-Exchange Resin To a 50 gram amount of mastic gum was added absolute ethanol (800 ML) and the mixture was left to stand for 24 hours. The mixture was shaken for 30 minutes at 150 rpm and left to stand for two hours. The obtained ethanol solution was decanted from insoluble material into a 3 L round bottom flask. To the insoluble material was added 400 ML of fresh ethanol and the mixture was shaken again 30 minutes at 150 rpm and was left to stand for 30 minutes. The obtained ethanol solution was decanted and added to the first ethanol solution. This step was repeated once more using 200 ML absolute ethanol. This gave 1.4 L of ethanol solution. The ethanol was evaporated using a rotary evaporator, and to the remaining material was added n-hexane (1.2 Liter) and the mixture was shaken at 150 rpm for 4 hours. It was then left to stand for 4 hours and the hexane solution was decanted from insoluble material into a 3 L Erlenmeyer. To the remaining insoluble material was added 800 ML fresh hexane and the mixture was shaken for 6 hours at 150 rpm and left to stand for 12 hours. The hexane solution was decanted into the 3 L Erlenmeyer flask containing the first 1.2 L of hexane solution. The hexane was evaporated in a clean 3 L round bottom flask to give about 30 grams of extract. (Yields range typically from 50-70% depending on the age and particle size of the used Mastic gum.)

The obtained extract was dissolved in ethanol (0.5 L) and treated with 100 grams of a strongly basic ion-exchange resin (e.g. Dowex-1X8-400; Amberlite IRA 400; Diaion SA10A) on a shaker. The ion-exchange resin was filtered off and washed with methanol until TLC did not show any significant spots. The resin was then treated with 10% ethanolic acetic acid solution in order to release the carboxylic acids from the resin. The ethanolic acetic acid mixture was evaporated to yield the isolated carboxylic acid fraction. Typical yields are around 50% of the starting extract (15 grams). This particular isolated acidic fraction obtained from mastic gum as described hereinabove is termed "Acidic Mixture 3" or "Acidic-3".

For comparison, addition of hexane to the acidic fraction as prepared according to the teaching of WO2003/092712 or Parachos et al, (2007), Antimacrobial Agents and Chemotherapy, 51(2), 551, showed that a substantial amount of that acidic fraction was insoluble in hexane.

Example 2. Preparation of Different Formulations in Cottonseed Oil

Example 2A: A 5% (w/w) Composition of an Isolated Acidic Fraction of Mastic Gum in USP/NF Grade Cottonseed Oil To 1 gram of the obtained isolated acidic fraction from Example 1A ("Acidic-1") was added 19 grams of cottonseed oil (USP/NF) was added and the mixture was shaken at 150 rpm until a clear and homogeneous composition was obtained (ca. 2 hours).

In the same way, cottonseed oil formulations can be prepared from the isolated acidic fractions obtained from Examples 1B-1F.

2B: Cottonseed Oil Formulations Prepared from Individual Triterpenoic Acids

General procedure: The desired amounts of triterpenoic acids are weighed into a round-bottom flask and the mixture is dissolved in a suitable solvent. Non-limited examples of suitable solvents are diethyl ether, dichloromethane and ethanol. To this solution is added the desired amount of cottonseed oil. The solvent is evaporated from the obtained mixture, providing the cottonseed oil formulation of triterpenoic acids.

As a specific example, 200 mg each of MDA and IMDA are dissolved in 30 ML diethyl ether in a 100 ML round bottom flask. To the clear solution is added 19.6 grams of cottonseed oil, and the mixture is stirred for a few minutes for homogenization. The diethyl ether is removed from the mixture using a rotary evaporator, providing 20 grams of a formulation of 1% (w/w) each of MDA and IMDA in cottonseed oil. Further traces of diethyl ether may be removed via high-vacuum treatment of the formulation.

Using this general procedure, the formulations (compositions) shown in Table 1 were prepared.

TABLE 1

Formulations of triterpenoic acids in cottonseed oil prepared by general procedure of Example 2B

| Formulation | Cmpd. 1 | Cmpd. 2 | Cmpd. 3 | Cmpd. 4 | Cmpd. 5 | Cmpd. 6 |
|---|---|---|---|---|---|---|
| 1 | 3-OAc-MLA | 3-OAc-IMLA | MDA | IMDA | OA | MA |
| 2 | 3-OAc-MLA | 3-OAc-epi-IMLA | MDA | IMDA | OA | MA |
| 3 | 3-OAc-epi-MLA | 3-OAc-IMLA | MDA | IMDA | OA | MA |
| 4 | 3-OAc-epi-MLA | 3-OAc-epi-IMLA | MDA | IMDA | OA | MA |
| 5 | 3-OAc-MLA | 3-OAc-epi-IMLA | MDA | IMDA | OA | |
| 6 | 3-OAc-epi-MLA | 3-OAc-IMLA | MDA | IMDA | OA | |
| 7 | 3-OAc-epi-MLA | 3-OAc-epi-IMLA | MDA | IMDA | OA | |
| 8 | 3-OAc-MLA | 3-OAc-epi-IMLA | MDA | IMDA | | |
| 9 | 3-OAc-epi-MLA | 3-OAc-IMLA | MDA | IMDA | | |
| 10 | 3-OAc-epi-MLA | 3-OAc-epi-IMLA | MDA | IMDA | | |
| 11 | 3-OAc-MLA | 3-OAc-epi-IMLA | | | | |
| 12 | 3-OAc-epi-MLA | 3-OAc-IMLA | | | | |
| 13 | 3-OAc-epi-MLA | 3-OAc-epi-IMLA | | | | |
| 14 | MDA | IMDA | OLN | MA | | |
| 15 | MDA | IMDA | OLN | | | |

TABLE 1-continued

Formulations of triterpenoic acids in cottonseed oil prepared by general procedure of Example 2B

| Formulation | Cmpd. 1 | Cmpd. 2 | Cmpd. 3 | Cmpd. 4 | Cmpd. 5 | Cmpd. 6 |
|---|---|---|---|---|---|---|
| 16 | MDA | IMDA | | | | |
| 17 | MDA | IMDA | MLA | IMLA | | |
| 18 | MDA | IMDA | MLA | | | |
| 19 | MDA | IMDA | IMLA | | | |
| 20 | 3-OAc-MLA | 3-OAc-epi-IMLA | IMDA | | | |
| 21 | 3-OAc-epi-MLA | 3-OAc-IMLA | IMDA | | | |
| 22 | 3-OAc-epi-MLA | 3-OAc-epi-IMLA | IMDA | | | |
| 23 | 3-OAc-MLA | 3-OAc-epi-IMLA | MDA | | | |
| 24 | 3-OAc-epi-MLA | 3-OAc-IMLA | MDA | | | |
| 25 | 3-OAc-epi-MLA | 3-OAc-epi-IMLA | MDA | | | |

It is clear to a person skilled in the art that this procedure can be used to make additional formulations of triterpenoic acids in cottonseed oil. In addition, it is also clear to a person skilled in the art that instead of cottonseed oil other suitable oils and hydrophobic carriers can be used with this procedure to prepare the corresponding formulations of triterpenoic acids.

Example 3A. Isolation and Chemical Characterization of Isolated Acidic Fraction of Mastic Gum Mastic resin from *Pistacia lentiscus* L. was extracted according to any of the methods described Examples 1A-1F to obtain the fraction which was analyzed by reversed phase HPLC in order to identify the major constituents. The HPLC analysis is consistent with the presence the isolated fraction of moronic acid and oleanonic acid in the isolated fraction, on the basis of comparison with analytical standards.

In order to isolate and determine the structure of further main constituents of the isolated acidic fraction, a preparative HPLC method was developed. Using this method, six major constituents of the isolated acidic fraction (For example "Acidic-1" obtained according to Example 1A) were subsequently isolated by preparative HPLC. A preparative HPLC method was developed on a 30×250 mm preparative column (ACE-121-2530). Samples of the isolated fraction (ca. 75 mg per run) were injected using a 5 ML loop.

Identified compounds include such compounds as, moronic acid, oleanonic acid, masticadienonic acid, isomasticadienonic acid, 3-OAcetyl-masticadienolic acid, and 3-O-acetyl-isomasticadienolic acid, 3-O-acetyl-epimasticadienolic acid, 3-O-acetyl-epi-isomasticadienolic acid, masticadienolic acid and isomasticadienolic acid.

Further isolation efforts yielded several additional minor constituents (<5% of isolated fraction), whose presence varied in isolated acidic fraction preparations from different mastic gum batches. The following minor constituent compounds may or may not be present in the isolated acidic fractions:

MLA: 3-beta-masticadienolic acid
IMLA: 3-beta-isomasticadienolic acid
Epimasticadienolic acid (3-alpha-masticadienolic acid)
Epi-isomasticadienolic acid (3-alpha-isomasticadienolic acid)
Dihydromasticadienonic acid
Dihydroisomasticadienonic acid Example 3B Synthesis of Some Triterpenoic Acids Found in the Isolated Acidic Fractions of Mastic Gum Oleanonic Acid (OA)

Oleanonic acid was obtained in three steps from commercially available oleanolic acid.

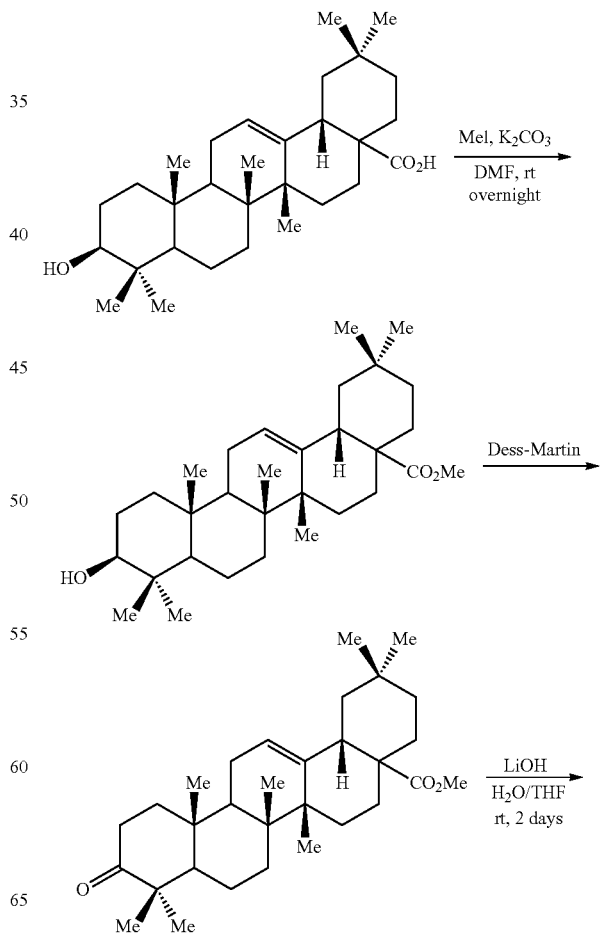

-continued

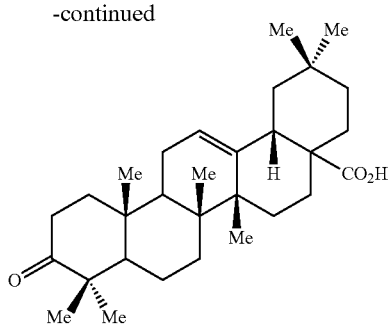

Oleanolic acid was first converted to the corresponding methyl ester by treatment with methyl iodide and potassium carbonate in dimethylformamide (DMF). Oxidation of oleanolic acid methyl ester to oleanonic acid methyl ester was performed using Dess-Martin periodane reagent in dichloromethane (DCM). Hydrolysis of oleanonic acid methyl ester with lithium hydroxide in aqueous THF gave upon acidification the desired oleanonic acid.

Masticadienonic Acid (MLA)

Masticadienonic acid (500 mg) was dissolved in methanol (30 ML) and cooled to 0° C. NaBH$_4$ (83 mg; 2.0 eq.) was added and the mixture was stirred overnight at room temperature. After TLC (hexane:ethylacetate) showed full conversion, the reaction mixture cooled to 0° C. and quenched by addition of 20 ML cold water. The methanol was evaporated from the mixture, which was then extracted with diethyl ether. The crude product was purified by column chromatography over silica gel (DCM:MeOH=95:5 to 90:10) to give MLA as white solid (400 mg; 80%).

Isomasticadienolic Acid (IMLA)

Isomasticadienonic acid (500 mg) was dissolved in methanol (30 ML) and cooled to 0° C. NaBH$_4$ (83 mg; 2.0 eq.) was added and the mixture was stirred overnight at room temperature. After TLC (hexane:ethylacetate) showed full conversion, the reaction mixture cooled to 0° C. and quenched by addition of 20 ML cold water. The methanol was evaporated from the mixture, which was then extracted with diethyl ether. The crude product was purified by column chromatography over silica gel (DCM:MeOH=95:5 to 90:10) to give IMLA as white solid (420 mg; 82%).

3-OAc-MLA

MLA (400 mg) was dissolved in anhydrous pyridine (5 ML), and acetic anhydride (160 mg; 3.55 eq.) was added in one portion. The mixture was stirred overnight at room temperature and monitored by TLC (hexane/ethylacetate). The reaction mixture was diluted with ethylacetate (15 ML) and 1M aqueous HCl (20 ML) and the mixture was stirred vigorously for 1 hour. The layers were separated, the organic layer was dried over MgSO$_4$ and evaporated. The crude product was purified by column chromatography over silicagel (hexane/ethylacetate=10:1 to 9:1) to yield 3-OAc-MLA as a white solid (220 mg; 55%).

3-OAc-IMLA

IMLA (400 mg) was dissolved in anhydrous pyridine (5 ML), and acetic anhydride (160 mg; 3.55 eq.) was added in one portion. The mixture was stirred overnight at room temperature and monitored by TLC (hexane/ethylacetate). The reaction mixture was diluted with ethylacetate (15 ML) and 1M aqueous HCl (20 ML) and the mixture was stirred vigorously for 1 hour. The layers were separated, the organic layer was dried over MgSO$_4$ and evaporated. The crude product was purified by column chromatography over silicagel (hexane/ethylacetate=10:1 to 9:1) to yield 3-OAc-IMLA as a white solid (190 mg; 47%).

3-OAc-epi-MLA

MLA (400 mg) was dissolved in anhydrous pyridine (5 ML), and acetic anhydride (160 mg; 3.55 eq.) was added in one portion, followed by 4-N,N-dimethylaminopyridine (DMAP; 20 mg). The mixture was stirred overnight at room temperature and monitored by TLC (hexane/ethylacetate). The reaction mixture was diluted with ethylacetate (15 ML) and 1M aqueous HCl (20 ML) and the mixture was stirred vigorously for 1 hour. The layers were separated, the organic layer was dried over MgSO$_4$ and evaporated. The crude product was purified by column chromatography over silicagel (hexane/ethylacetate=10:1 to 9:1) to yield a mixture of 3-OAc-MLA and 3-OAc-epi-MLA as a white solid (330 mg; %). The isomers were separated using preparative HPLC to provide 3-OAc-epi-MLA (120 mg) as a white solid.

3-OAc-epi-IMLA

IMLA (400 mg) was dissolved in anhydrous pyridine (5 ML), and acetic anhydride (160 mg; 3.55 eq.) was added in one portion, followed by 4-N,N-dimethylaminopyridine (DMAP; 20 mg). The mixture was stirred overnight at room temperature and monitored by TLC (hexane/ethylacetate). The reaction mixture was diluted with ethylacetate (15 ML) and 1M aqueous HCl (20 ML) and the mixture was stirred vigorously for 1 hour. The layers were separated, the organic layer was dried over MgSO$_4$ and evaporated. The crude product was purified by column chromatography over silicagel (hexane/ethylacetate=10:1 to 9:1) to yield a mixture of 3-OAc-IMLA and 3-OAc-epi-IMLA as a white solid (310 mg; %). The isomers were separated using preparative HPLC to provide 3-OAc-epi-IMLA (110 mg) as a white solid.

Epi-MLA and epi-IMLA were prepared by hydrolysis of the corresponding acetates with LiOH in aqueous THF. Standard work-up provided the compounds in respective yields of 45% and 53% as white solids.

Dihydromasticadienonic acid and dihydroisomasticadienonic acid can be prepared according to D. Barton, E. Seoane. J. Chem. Soc. 1956, 4150; and E. Seoane ibid. 4158.

Example 4—Effect of Using Isolated Acidic Fractions and/or Specific Triterpenooïs Compounds of the Isolated Acidic Fraction Compositions of the Invention on Retinal Ganglion Cells (RGC) Upon Optic Nerve Axotomy Axotomy of the optic nerve is performed on the right eye of deeply anesthetized rats (19 rats per group). The test groups receive a sub-dermal injection in the posterior neck area of various tested compositions (0.025 ml/injection), and the control group is similarly injected with the same volume of vehicle. The first injection is given to all the animals directly after surgery. Subsequent injections (same dosage and method of administration) are administered twice a week, every 3 to 4 days.

Fourteen days after axotomy, a fluorescent retrograde neurotracer (Di-Asp) is inserted into the axotomized optic nerve in order to stain surviving Retinal Ganglion Cells (RGC), and 24 hours later, the rats are sacrificed in a CO$_2$ saturated chamber and the injured right eye is enucleated. The retinas are isolated, and flattened on a slide and fixed with xylene based mounting medium.

Whole-mount retinas are evaluated with a fluorescent microscope. Dyed cells are counted manually.

Compositions Used Include:
Isolated acidic fraction of mastic gum (for example "Acidic-1" from Example 1A and its corresponding cottonseed oil formulation prepared according to Example 2A),
The following compounds and combinations, prepared according to Example 2B, are tested:
OA: Oleanonic acid
MDA: Masticadienonic acid
IMDA: Isomasticadienonic acid
The following formulations were used for injection:
Vehicle: cottonseed oil
IMDA: 1% % (w/w) in cottonseed oil
MDA: 1% % (w/w) in cottonseed oil
IMDA and MDA: each 1% % (w/w) in cottonseed oil
IMDA, MDA and OA: each 1% % (w/w) in cottonseed oil Example 5—Retinal Detachment (RD) Model—Effect of Using Isolated Acidic Fractions and/or Specific Triterpenoids Compounds of the Isolated Acidic Fraction Compositions of the Invention Retinal detachment (RD) is performed on the right eye of deeply anesthetized animals (xylazine 50 mg/kg and ketamine 35 mg/kg) following dilatation of the pupil with Tropicamide drops 0.5%. RD is induced through the generation of a small opening in the retina at the ora serata followed by a sub-retinal injection of 5 µl saline with a 30 G syringe needle. Approximately half of the retinal area is detached by this procedure.

Rats with RD are divided into six experimental groups, five test groups receiving a sub-dermal injection in the posterior neck area of pharmaceutical compositions as disclosed in Example 4, and the control group injected is administered with the same volume of vehicle. The first injection is given to all the animals directly after surgery. The second injection (same dosage and method of administration) is administered 48 hours after surgery.

On days 3 and 14 days after RD, the operated rats are euthanized in a $CO_2$ saturated chamber. The injured right eye and the untreated left eye are enucleated. The retinas are isolated, frozen on dry ice and processed for Western blot analysis or immunohistochemical analysis. The left eye retinas serve as non-operated controls.

The expression levels of Semaphorin3A (Sema3A), Neuropilin1 (NP1), and GAP43 are determined. Caspase3 is used as an apoptotic marker, and morphological changes in Müller and microglial cells are examined.

The morphological changes of the Muller cells are studied by staining for glial fibrillary acidic protein (GFAP). GFAP labels Muller cells in the retina, and is commonly used as a stress indicator. Microglial invasion and activation are regarded as harmful or beneficial to neurons. Microglial activation after acute CNS injury is primarily a reactive and adaptive glial cell response, which is triggered by injured neurons and which is designed to ameliorate primary tissue damage and to promote subsequent repair and gliosis (glial scar) as a result. Microglia become activated in the retina usually after injury, stimulate and recruit endothelial cells and fibroblasts. Immunohistochemical analysis of sections of detached and non-injured retinas labeled with IB4 and stained with the nuclear dye PI are used to identify any signs of activated microglial cells in the retina.

Example 6: rAION, a Rodent Model of NAION (Nonarteritic Anterior Ischemic Optic Neuropathy)—Effect of Isolated Acidic Fractions and/or Specific Triterpenoids Compounds of the Isolated Acidic Fraction Compositions of the Invention Optic nerve ischemia effected by NAION results in myelin and axonal damage. In the rodent model of NAION (rAION), the optic nerve ischemia (in anesthetized rats) is laser-induced using a nd-YAG laser at 532 nm with 500 micron spot size and 50 mW power with 1 second pulses. This results in optic nerve ischemia without causing direct thermal damage. The induction results in postinfarct demyelation and oligodendricyte death in the following days. Demyelation results in the release of soluble factors that can inhibit axonal regeneration. These factors include myelin-associated glycoprotein (MAG) and NOGO66. These factors activate the axonal membrane protein complex (LINGO-1), which in turn activates the axonal kinase RAS homolog A (RhoA) via phosphorylation. Activated RhoA inhibits cytoskeleton polymerization, which results in axonal growth cone collapse.

Animals are divided over several groups with 10-12 animals per group.

Three days post-induction, treatment of the animal groups with the different compositions of the invention and placebo control (as detailed in Example 4) is commenced. A twice-weekly regimen with 50 microliter subcutaneous injections is applied. Treatment is elicited for 28 days or 56 days.

Improvement of axonal regeneration is detected by GAP43 immunostaining. Optic nerve ultrastructure is evaluated after treatment in order to detect myelation profiles of different axon fiber sizes. Results of treatment and placebo groups are compared.

Example 7—In Vitro Glaucoma Model—Effect of Various Compositions

Primary acutely dissociated retinal cell culture are prepared from adult Wistar rats. The neuroprotective effects of the test compositions (combinations) on RGC survival is determined by pre-treatment prior to trophic factor withdrawal. Cell viability is assessed by double-label immunocytochemistry.

Adult Wistar rats are euthanized and retinal cell suspensions are prepared by dissecting the retinas and incubating (37° C., 30 min) in digestion buffer containing neurobasal medium supplemented with 2 mg/mL papain, 0.4 mg/mL dl-cysteine, and 0.4 mg/mL bovine serum albumin (BSA).

Retinas are processed in order obtain a suspension of single cells. Retinal cells are seeded on poly-d-lysine- and laminin-coated 8-well culture slides at a density of approximately $1 \times 10^6$ cells/well with 0.5 mL/well RGC culture medium and cultured in 95% air and 5% $CO_2$ at 37° C. for 3 days.

Cells are treated with either test composition or vehicle (control) immediately after dissociation and exposed to RGC culture medium as above, but without BDNF, CNTF, and bFGF (TFW RGC medium).

TABLE 2

| Condition | Media | Drug treatment |
| --- | --- | --- |
| Control (3 technical replicates) | Complete RGC medium | N/A |

TABLE 2-continued

| Condition | Media | Drug treatment |
| --- | --- | --- |
| Test compound (12 compounds, 3 technical replicates each) | Complete RGC medium | Test compound |
| Control (3 technical triplicates) | TFW RGC medium | N/A |
| Test compounds (12 compounds, 3 technical replicates and 2 concentrations each) | TFW RGC medium | Test compound |
| Test compound specific vehicle (3 technical replicates per vehicle) | TFW RGC medium | Vehicle |

On Day 3, cultures of retinal cells are subjected to double-label immunocytochemistry. Cultures are immunoreacted with primary antibodies against Thy-1 and neurofilament-1 68 kDa. Cells are co-labelled with DAPI to visualize nuclei.

Healthy RGCs are identified based on double-positive immunoreactivity for both Thy-1 and neurofilament-1 68 kDa, as well as the following four morphological criteria: presence of continuous membranes; no signs of vacuolation; no signs of perikaryal swelling; and no signs of nuclear pyknosis or fragmentation. Cells are counted manually.

Example 8—Treatment of Glaucoma Using Various Compositions of the Invention

Various compositions are tested for their efficacy in Glaucoma treatment in rats. Glaucoma symptoms are induced in rats by intraocular (intravitreal) injection of excitotoxic agents such as N-methyl-d-aspartate (NMDA), alpha-amino-3-hydroxy-5-methyl-4-isoxazoleproprionic acid (AMPA) or kainic acid, or by other means, such as, photocoagulation, for example, by irradiation with a laser beam. These agents induce degenerative conditions in the eye that are similar to glaucoma. The extent to which the compositions of the invention are able to ameliorate and/or reverse the degenerative symptoms caused by the excitotoxic agents is a measure of their effect in the treatment of glaucoma.

Degeneration of retinal ganglion cells (RGCs) in human and experimental glaucoma is accompanied by a neuroinflammatory process involving retinal microglial cells and increased production of inflammatory mediators. In addition, early and exacerbated activation of retinal microglial cells has been proposed to contribute to the degenerative process, suggesting that the control of microglia reactivity can prevent the glaucomatous loss of RGCs. A wide variety of animal models of glaucoma including pigs, dogs, monkeys and rodents, most of these models involve optic nerve damage mediated through ocular hypertension. Other established models available to study glaucoma rely on RGC induced-death upon genetic mutations, mechanical trauma to the optic nerve, toxic insult to retinal neurons, or the induction of retinal ischemia.

In this study the rat laser photocoagulation (GL) model is used in order to evaluate the neuroprotective and neuroregenerative effects of the tested compositions.

Study Design:

Briefly, high IOP is unilaterally induced by laser photocoagulation of episcleral veins on day 0 and day 7. The contralateral eye serves as control. The compositions are delivered subcutaneously (s.c) twice a week starting on day 1 only in animals with IOP of 16 mmHg or higher. IOP is monitored on the next day after the lasering (study day 1), on day 4, day 7 and once a week afterwards. The function of retinal ganglion cells (RGCs) is evaluated in vivo using pattern electroretinography (pERG) at the baseline, on day 14 and on day 28. Measurements at day 28 serve as milestone decision for an optional follow-up period of 2-4 weeks, at the end of which an additional pERG measurement is performed. The retinas and optic nerves are collected and processed for retinal ganglion cell counts and optic nerve axon counts. In addition, immunohistochemical evaluation of retinal tissue is performed for markers of inflammation. The following treatment arms (n=12 rats in each arm) are used:

Group 1: Naïve rats (n=12); (Naïve)
Group 2: Vehicle-treated GL model (n=12); (Vehicle)
Group 3: Test formulation 1-treated GL model (n=12); Composition D (MDA (1% w/w)+IMDA (1% w/w)) prepared as described in Example 2B.
Group 4: Test formulation 2-treated GL model (n=12); Composition E (Acidic Mixture 1 ("Acidic-1") of Example 1A, as a 2.5% (w/w) formulation in cottonseed oil, prepared as described in Example 2A)

Materials and Methods

Rat Glaucoma Model

Experimental increase in IOP was induced unilaterally by laser photocoagulation of episcleral veins as previously described (Kalesnykas et al., 2007, Neuroscience 150: 692-704). The contralateral eye serves as control. Five-to-seven months old Long Evans rats are used. The intraocular pressure (IOP) was monitored at the baseline, on the first day after lasering (day 1), day 4, day 7 and once a week for the remaining follow-up period. Only rats with IOP of 16 mmHg or higher as assessed on day 1 are admitted to the study groups.

Administration

The test compositions are administered subcutaneously (s.c.) twice a week starting from day 1.

pERG Measurements

Recordings were performed using Celeris system (Diagnosys LLC). A single drop of drop oxybuprocaine (Oftanucain®, Santen, Finland) was applied to the cornea for local anesthesia. Animals were placed on a controlled heating-pad to maintain body temperature at approximately 37° C.

Animal Sacrifice and Tissue Collection

At the end of the study, the rats were sacrificed by transcardial perfusion first with 0.9% NaCl solution, then with 4% paraformaldehyde in 0.1M phosphate buffer solution, pH 7.4. The eyeballs and optic nerves (n=4 rats from each group, collected in a randomized manner) were collected and embedded into optimal cutting temperature (OCT) for cryosectioning/retinal whole mounts (n=8 rats from each group) were prepared for further estimation of the total number of RGCs.

Morphological Assessment of Optic Nerves

After the optic nerves (from 8 rats/treatment group) were postfixed in 4% PFA (in 0.1M phosphate buffer, pH 7.4) solution, they were placed in 1% osmium, dehydrated in ascending alcohol concentration and placed in 1% uranyl acetate in 100% ethanol for 1 hour (Cone et al., 2012. Exp Eye Res. June; 99:27-35; Ragauskas et at, 2014, PLoS One. 3; 9(12)). Then the optic nerves were embedded in epoxy resin mixture at 60° C. for 48 hours and semi-thin sections (1 μm-thick) of optic nerves were serially sectioned through the optic nerve damage site. Optic nerve damage/number of axons was estimated under the light microscope.

Results:

pERG measurements (recordings) that reflect functionality of RGCs were performed at follow-up days 14 and 28. The results presented below in Table 3 and in the bar graphs shown in FIG. 1, demonstrate that treatment with the indicated combinations exhibit an increase in mean amplitude on both follow up days, as compared to the vehicle-treated group.

TABLE 3

Lasered eye relative increase in mean amplitudes at the follow-up day, 28 adjusted to baseline.

| Treatment group | Relative increase in mean amplitude on day 28, % (Compared to Vehicle) |
|---|---|
| D | 24.0% |
| E | 18.8% |

Figure 2:
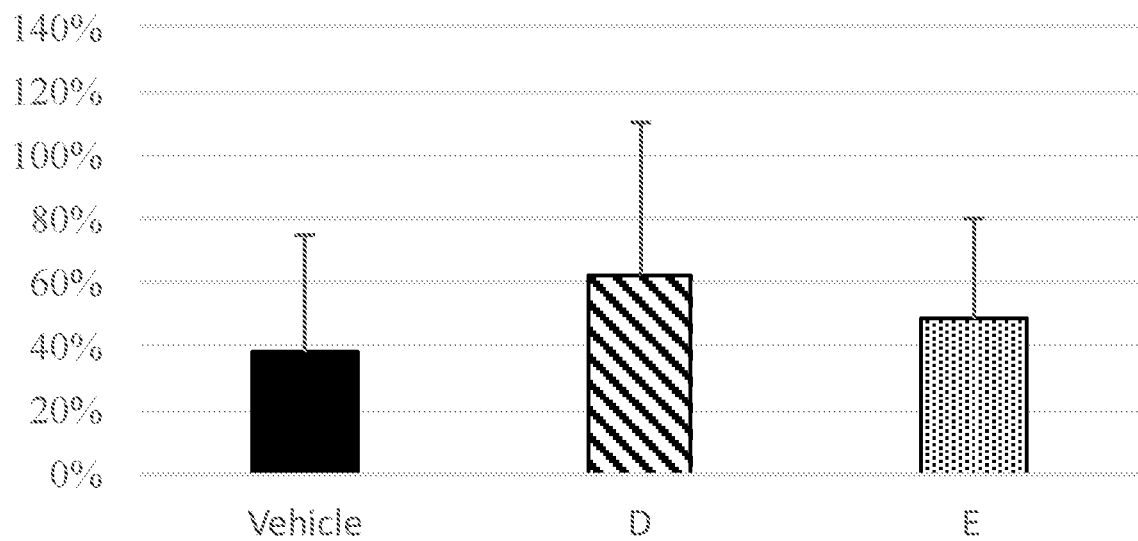
FIG. 2—Bar Graphs showing Brn3a+ RGC counts in whole-mounted retina.

Analysis of the total number of Brn3-a positive RGCs (relative to Naïve rats). revealed an effect of the tested compositions. For example, rats treated with the tested compositions had a higher RGC count as compared to the vehicle-treated group (FIG. 2). Higher number of Brn3a-positive cell is indicative of lower cell loss, wherein the cell loss is triggered by the Laser photocoagulation. These results are in line with the pERG measurements results and supports neuroprotective effect of the test compositions on RGC survival.

Figure 3:
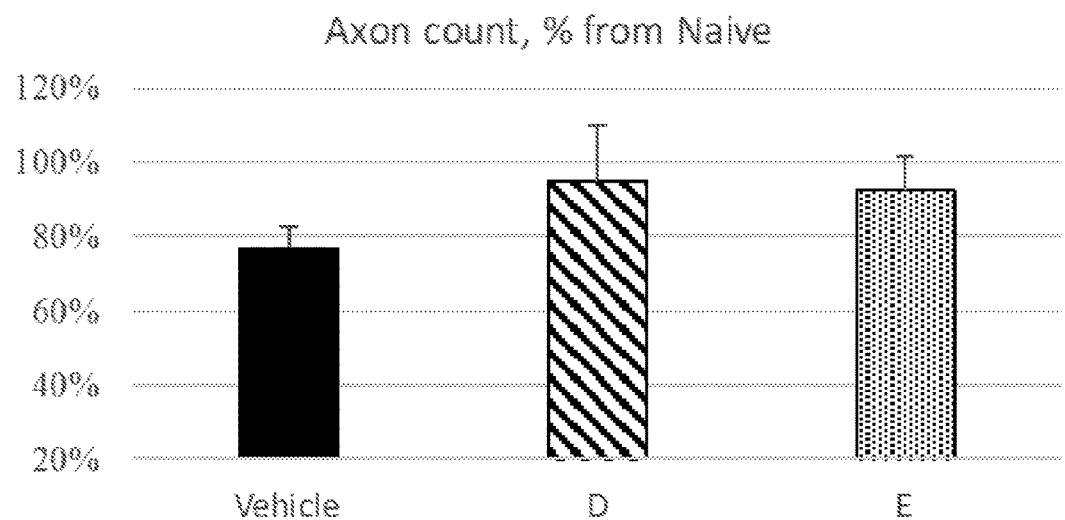
FIG. 3—Bar graphs showing number of optic nerve axons per optic nerve area in various treated rat groups, compared to naïve rats (%)
Figure 4:
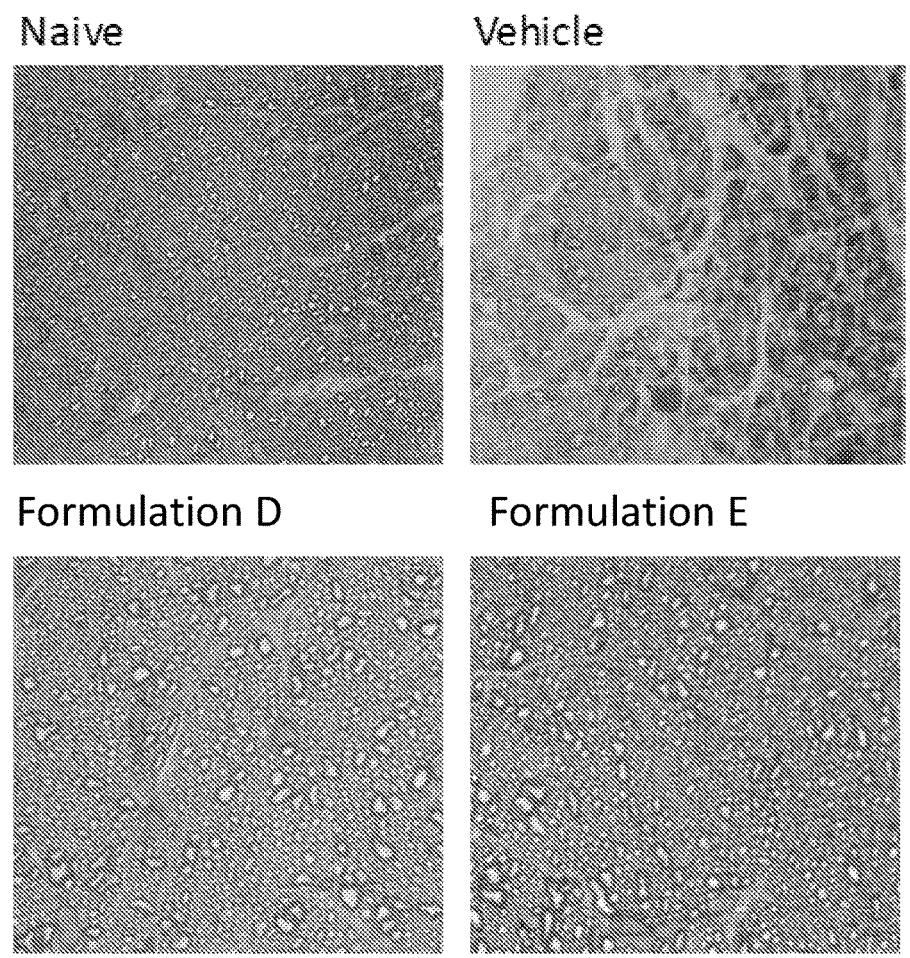
FIG. 4—Images of semi-thin cross-sections of optic nerves obtained from rats treated with the indicated formulations (D, E), vehicle treated or non-treated rats (Naïve).

Next, optic nerve axon in samples from the tested rats were counted under the light microscope, to estimate the optic nerve damage. The results are presented in FIG. 3. As shown, administration of test compositions D and E tend to protect axons from degeneration triggered by Laser photocoagulation Further supporting results demonstrating the protective effect of the tested compositions can be seen in FIG. 4, which show representative images of semi thin sections of the optic nerves. The results clearly demonstrate differences in the degeneration processes between the treated groups and vehicle treated group (FIG. 4).

CONCLUSIONS

The study presented herein demonstrates the neuroprotective and neurodegenerative effect of the tested compositions in treating glaucoma.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method of treating an optic neuropathy condition in a subject in need thereof, the method comprising administering a composition comprising an effective amount of an isolated acidic fraction of mastic gum, and a pharmaceutically acceptable carrier, wherein the fraction is characterized in that it is soluble in at least one polar organic solvent and in at least one non-polar organic solvent, and wherein said fraction is substantially devoid of compounds which are soluble in said polar organic solvent but insoluble in said non-polar organic solvent, wherein the isolated acidic fraction comprises at least two of: masticadienolic acid, masticadienonic acid, isomasticadienonic acid, isomasticadienolic acid, 3-O-acetyl-masticadienolic acid, 3-O-acetyl-epimasticadienolic acid, 3-O-acetyl-isomasticadienolic acid, 3-O-acetyl-epi-isomasticadienolic acid, oleanonic acid and moronic acid, wherein the optic neuropathy condition is traumatic neuropathy, ischemic neuropathy, radiation optic neuropathy (RON), optic neuritis, compressive optic neuropathy, infiltrative optic neuropathy, mitochondrial optic neuropathy, nutritional optic neuropathies, toxic optic neuropathies, hereditary optic neuropathy, or a combination thereof.

2. The method according to claim 1 wherein the acidic fraction is obtained from an isolated fraction of mastic gum that is soluble in at least one polar organic solvent and at least one non-polar organic solvent by an acid-base extraction, thereby separating the isolated acidic fraction from the non-acidic fraction of mastic gum that is soluble in at least one polar organic solvent and one non-polar organic solvent.

3. The method according to claim 1, wherein the optic neuropathy condition is ischemic neuropathy.

4. The method according to claim 3, wherein the ischemic optic neuropathy is selected from: Nonarteritic Ischemic Optic neuropathy (NAION), Anterior ischemic optic neuropathy (AION) and Posterior ischemic optic neuropathy.

5. The method according to claim 1, wherein the optic neuropathy condition results from a storage disease, causing the deposition of lipoprotenaceous substances in the optical nerve.

6. The method according to claim 1, wherein the composition is administered by parenteral route, selected from the group consisting of intravenous, intramuscular, subcutaneous, intradermal, intraperitoneal, intraarterial, intrauterine, intraurethral, intracardial, intracerebral, intracerebroventricular, intrarenal, intrahepatic, intratendon, intraosseous, intraocular and intrathecal.

7. The method according to claim 1, wherein the polar organic solvent is selected from the group consisting of methanol, ethanol, propanol, isopropanol, 1-butanol, 2-butanol, sec-butanol, t-butanol, 1-pentanol, 2-pentanol, 3-pentanol, neopentanol, 3-methyl-1-butanol, 2-methyl-1-butanol, 3-methyl-2-butanol, 2-methyl-2-butanol, ethyleneglycol, ethyleneglycol monomethyl ether, diethyl ether, methylethyl ether, ethylpropyl ether, methylpropyl ether, 1,2-dimethoxyethane, tetrahydrofuran, dihydrofuran, furan, pyran, dihydropyran, tetrahydropyran, methyl acetate, ethyl acetate, propyl acetate, acetaldehyde, methylformate, ethylformate, ethyl propionate, methyl propionate, dichloromethane, chloroform, dimethylformamide, acetamide, dimethylacetamide, N-methylpyrrolidone, acetone, ethylmethyl ketone, diethyl ketone, acetonitrile, propionitrile, and combinations thereof.

8. The method according to claim 1, wherein the non-polar organic solvent is selected from the group consisting of C5-C10 alkanes, C5-C10 cycloalkanes, C6-C14 aromatic hydrocarbons and C7-C14 perfluoroalkanes, and combinations thereof.

9. The method according to claim 1 wherein the composition comprises from about 0.01 to about 50% (w/w), or about 0.01 to about 12% (w/w), of the isolated acidic fraction of mastic gum, based on the total weight of the composition.

10. The method according to claim 1, wherein the composition is obtained by a process comprising the steps of:
  (a) treating the mastic gum with a polar organic solvent;
  (b) isolating a fraction soluble in said polar organic solvent;
  (c) optionally removing said polar organic solvent;
  (d) treating the soluble fraction obtained in step (b) or (c) with a non-polar organic solvent,
  (e) isolating a fraction soluble in said non-polar organic solvent;
  (f) optionally removing said non-polar organic solvent;
  (g) dissolving the fraction obtained in step (f) in an organic solvent;
  (h) treating the solution obtained in step (g) with a basic aqueous solution so as to obtain a basic aqueous fraction; and
  (i) acidifying the basic aqueous fraction obtained in step (h) with an acid solution so as to obtain an acidified aqueous solution.

11. The method according to claim 10, wherein the process further comprises the steps of:
  (j) extracting the acidified aqueous fraction obtained in step (i) with an organic solvent;
  (k) optionally contacting the organic fraction obtained in step (j) with a drying agent so as to remove remaining water;
  (l) removing organic solvent and/or excess acid from the fraction obtained in any of steps (i), (j) or (k); and
  (m) dissolving the isolated fraction obtained in step (l) in a pharmaceutically acceptable carrier.

12. The method according to claim 11, wherein steps (a) to (c) are carried out prior to steps (d) to (f); or wherein steps (d) to (f) are carried out prior to steps (a) to (c).

13. The method according to claim 10, wherein the polar organic solvent comprises ethanol, the non-polar organic solvent comprises hexane and the organic solvent for the acid-base extraction comprises diethyl ether.

14. The method according to claim 1, wherein the carrier is a hydrophobic carrier selected from the group consisting of at least one oil, at least one wax and combinations thereof.

15. A method of treating an optic neuropathy condition, the method comprising administering a composition consisting essentially of a mixture of triterpenoids comprising at least two triterpenoic acids, selected from the group consisting of: masticadienonic acid, isomasticadienonic acid, isomasticadienolic acid, masticadienolic acid, 3-O-acetyl-masticadienolic acid, 3-O-acetyl-epimasticadienolic acid, 3-O-acetyl-isomasticadienolic acid, 3-O-acetyl-epi-isomasticadienolic acid, oleanonic acid, moronic acid and combinations thereof; and a pharmaceutically acceptable carrier, wherein the optic neuropathy condition is traumatic neuropathy, ischemic neuropathy, radiation optic neuropathy (RON), optic neuritis, compressive optic neuropathy, infiltrative optic neuropathy, mitochondrial optic neuropathy, nutritional optic neuropathies, toxic optic neuropathies, hereditary optic neuropathy, or a combination thereof.

16. The method according to claim 15 consisting essentially of masticadienonic acid and isomasticadienonic acid.

17. The method according to claim 15 consisting essentially of masticadienonic acid; isomasticadienonic acid and oleanonic acid.

18. The method according to claim 15, wherein the optic neuropathy condition is ischemic neuropathy.

19. The method according to claim 18, wherein the ischemic optic neuropathy is selected from: Nonarteritic Anterior Ischemic Optic neuropathy (NAION), Anterior ischemic optic neuropathy (AION) and Posterior ischemic optic neuropathy.

20. The method according to claim 15, wherein the composition is in a form suitable for administration via parenteral route.

* * * * *